United States Patent
Sahin et al.

(10) Patent No.: US 11,701,413 B2
(45) Date of Patent: Jul. 18, 2023

(54) RNA FOR TREATMENT OF AUTOIMMUNE DISEASES

(71) Applicants: BioNTech SE, Mainz (DE);
TRON—Translationale Onkologie an der Universitätsmedizin der Johannes Gutenberg-Universität Mainz gemeinnützige GmbH, Mainz (DE)

(72) Inventors: Ugur Sahin, Mainz (DE); Sebastian Kreiter, Mainz (DE); Christina Krienke, Dienheim (DE); Jutta Petschenka, Mainz (DE); Lena Mareen Kranz, Mainz (DE); Mustafa Diken, Mainz (DE)

(73) Assignees: BioNTech SE, Mainz (DE);
TRON—Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 327 days.

(21) Appl. No.: 16/500,005

(22) PCT Filed: Apr. 10, 2018

(86) PCT No.: PCT/EP2018/059188
§ 371 (c)(1),
(2) Date: Oct. 1, 2019

(87) PCT Pub. No.: WO2018/189193
PCT Pub. Date: Oct. 18, 2018

(65) Prior Publication Data
US 2020/0061166 A1 Feb. 27, 2020

(30) Foreign Application Priority Data
Apr. 11, 2017 (WO) .................. PCT/EP2017/058651

(51) Int. Cl.
*A61K 39/00* (2006.01)
*A61P 37/06* (2006.01)
*C12N 15/11* (2006.01)
*C12N 15/117* (2010.01)

(52) U.S. Cl.
CPC .......... *A61K 39/0008* (2013.01); *A61P 37/06* (2018.01); *C12N 15/11* (2013.01); *C12N 15/117* (2013.01); *A61K 2039/53* (2013.01); *A61K 2039/55555* (2013.01); *C12N 2310/335* (2013.01)

(58) Field of Classification Search
CPC . A61K 39/0008; A61K 2039/53; A61P 37/06; C12N 15/11; C12N 15/117; C12N 2310/335
See application file for complete search history.

(56) References Cited

U.S. PATENT DOCUMENTS

| | | | |
|---|---|---|---|
| 2008/0108585 A1 | 5/2008 | Steinman et al. | |
| 2011/0143397 A1 | 6/2011 | Kariko et al. | |
| 2014/0370526 A1* | 12/2014 | Greenberg | ............... C12N 9/16 435/7.92 |
| 2015/0044244 A1* | 2/2015 | Wang | ................. A61K 39/0003 424/185.1 |
| 2016/0367704 A1* | 12/2016 | Fotin-Mleczek | .. A61K 48/0075 |
| 2017/0036889 A1 | 2/2017 | Ericson | |

FOREIGN PATENT DOCUMENTS

| | | |
|---|---|---|
| CN | 1703505 | 11/2005 |
| CN | 102947450 A | 2/2013 |
| RU | 2492234 C2 | 11/2011 |
| WO | WO2004024902 A1 | 3/2004 |
| WO | WO2007/024708 A2 | 1/2007 |
| WO | 2009050283 A1 | 4/2009 |
| WO | WO2011/071931 A2 | 6/2011 |
| WO | WO 2013/102203 A1 | 7/2013 |
| WO | WO 2013/120626 A1 | 8/2013 |
| WO | WO2014/160243 A1 | 10/2014 |
| WO | WO 2016/176330 A1 | 11/2016 |
| WO | WO-2017/036889 A1 | 3/2017 |
| WO | WO 2017/036889 A1 | 3/2017 |
| WO | WO 2017/182524 A1 | 10/2017 |
| WO | PCT/EP2018/059188 | 4/2018 |

OTHER PUBLICATIONS

Lobell et al: "Suppressive DNA Vaccination in Myelin Oligodendrocyte Glycoprotein Peptide-Induced Experimental Autoimmune Encephalomyelitis Involves a T1-Biased Immune Response", The Journal of Immunology, vol. 170, No. 4, (2003), pp. 1806-1813.
Sahin et al: "mRNA-based therapeutics—developing a new class of drugs", Nature Reviews Drug Discovery, vol. 13, No. 10, (2014), pp. 759-780.
Weiss, et al: "Prophylactic mRNA vaccination against allergy", Current Opinion in Allergy and Clinical Immuno, vol. 10, No. 6, (2010), pp. 567-574.
International Search Report and Written Opinion dated Jun. 20, 2018 by the International Searching Authority for International Application No. PCT/EP2018/059188, filed on Apr. 10, 2018 and published as WO 2018/189193 on Oct. 18, 2018 (Applicant—BIONTECH RNA Pharmaceuticals GmbH, et al.) (11 Pages).
International Preliminary Report on Patentability dated Oct. 15, 2019 by the International Searching Authority for International Application No. PCT/EP2018/059188, filed on Apr. 10, 2018 and published as WO 2018/189193 on Oct. 18, 2018 (Applicant—BIONTECH RNA Pharmaceuticals GmbH, et al.) (8 Pages).
Oliwia Andries et al; "N1-methylpseudouridine-incorporated mRNA outperforms pseudouridine-incorporated mRNA by providing enhanced protein expression and reduced immunogenicity in mammalian cell lines and mice", Journal of Controlled Release, vol. 217, Nov. 1, 2015 (Nov. 1, 2015), pp. 337-344.

(Continued)

*Primary Examiner* — J. E. Angell
(74) *Attorney, Agent, or Firm* — Ballard Spahr LLP

(57) ABSTRACT

The present invention relates to non-immunogenic RNA. This RNA forms the basis for the development of therapeutic agents for inducing tolerance towards an autoantigen and thus, for the treatment of autoimmune diseases.

Figure 1:
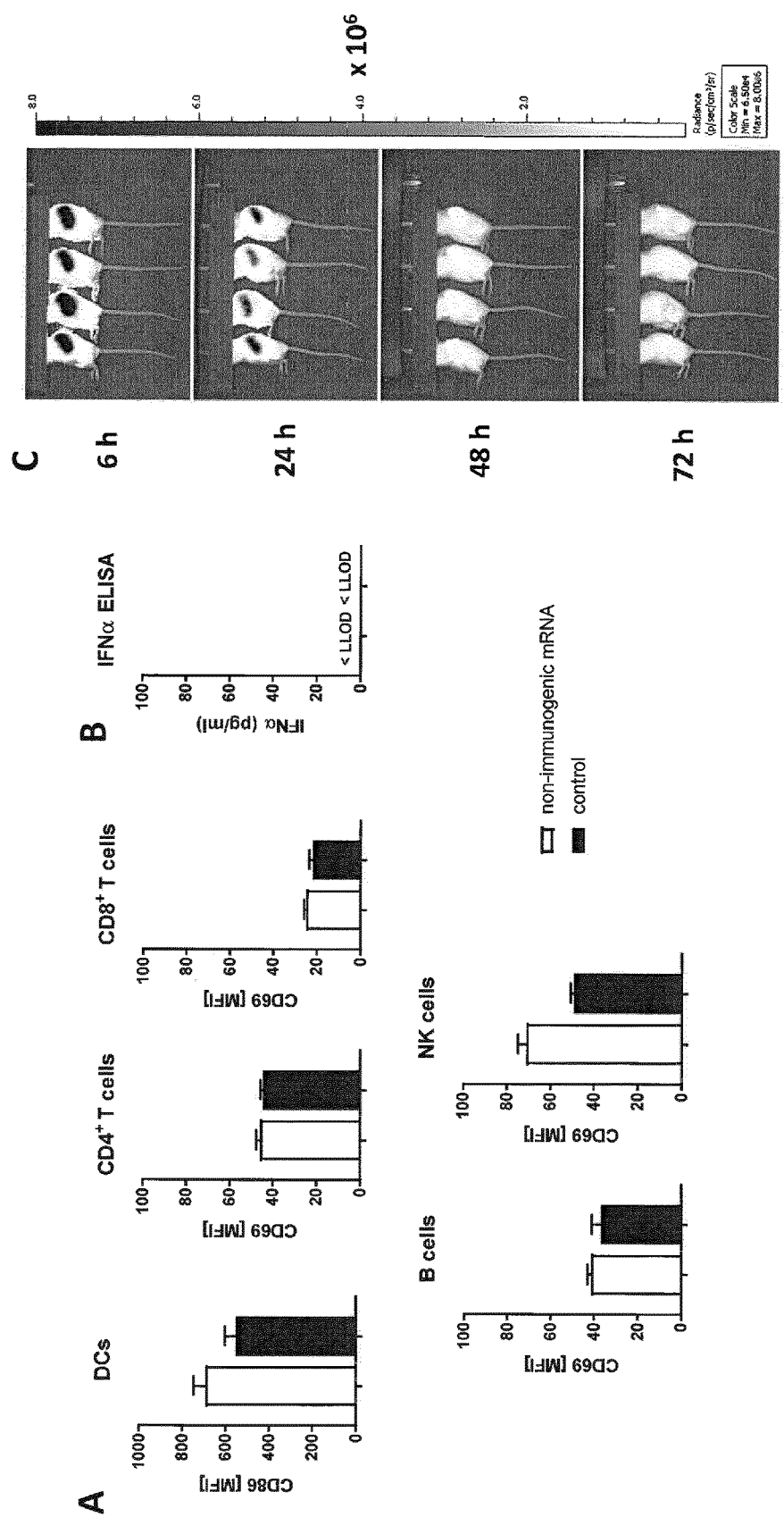

8 Claims, 21 Drawing Sheets
Specification includes a Sequence Listing.

(56) References Cited

OTHER PUBLICATIONS

Castillo, A., et al. "Rapid isolation of mycoviral double-stranded RNA from *Botrytis cinerea* and *Saccharomyces cerevisiae*", Virology Journal, 2011, vol. 8, p. 38.

Kariko, K., et al. "Generating the optimal mRNA for therapy: HPLC purification eliminates immune actication and improves translation of nucleoside-modified, protein-encoding mRNA", Nucleic Acids Research, vol. 39, No. 21, Sep. 2011, pp. 1-10.

Kariko, K., et al; "Suppression of RNA Recognition by Toll-like Receptors: The Impact of Nucleoside Modification and the Evolutionary Origin of RNA", Immunity, vol. 23, Aug. 2005, pp. 165-175.

Kariko, K., et al; "Incorporation of Pseudouridine into mRNA Yields Superior Nonimmunogenic Vector with Increased Translational Capacity and Biological Stability", Mol. Ther., vol. 16(11): 1833-40, Nov. 2008.

Kariko, K., et al; "Increased Erythropoiesis in Mice Injected with Submicrogram Quantities of Pseudouridine-containing mRNA Encoding Erythropoietin", Mol. Ther., vol. 20(5): 948-53, May 2012.

Creusot et al., A Short Pulse of IL-4 Delivered by DCs Electroporated With Modified Mrna Can Both Prevent and Treat Autoimmune Diabetes in NOD Mice; The American Society of Gene & Cell Therapy, vol. 18 no. 12, 2120 Dec. 2010.

Wang et al., Current Status of Non-Viral siRNA vectors for therapy of cancers, Journal of Pharm. Practice, 33(6) 498 (2015) (Abstract in English).

* cited by examiner

CD4+ T cells

MOG35-55 specific cells

SEQUENCE LISTING

<160> NUMBER OF SEQ ID NOS: 9

<210> SEQ ID NO 1
<211> LENGTH: 37
<212> TYPE: PRT
<213> ORGANISM: Artificial Sequence
<220> FEATURE:
<223> OTHER INFORMATION: Epitope

<400> SEQUENCE: 1

Ser Pro Gly Lys Asn Ala Thr Gly Met Glu Val Gly Trp Tyr Arg Ser
1               5                   10                  15

Pro Phe Ser Arg Val Val His Leu Tyr Arg Asn Gly Lys Asp Gln Asp
            20                  25                  30

Ala Glu Ala Gln Pro
        35

<210> SEQ ID NO 2
<211> LENGTH: 21
<212> TYPE: PRT
<213> ORGANISM: Artificial Sequence
<220> FEATURE:
<223> OTHER INFORMATION: Epitope

<400> SEQUENCE: 2

Met Glu Val Gly Trp Tyr Arg Ser Pro Phe Ser Arg Val Val His Leu
1               5                   10                  15

Tyr Arg Asn Gly Lys
            20

<210> SEQ ID NO 3
<211> LENGTH: 29
<212> TYPE: PRT
<213> ORGANISM: Artificial Sequence
<220> FEATURE:
<223> OTHER INFORMATION: Epitope

<400> SEQUENCE: 3

Ala His Ser Leu Glu Arg Val Cys His Cys Leu Gly Lys Trp Leu Gly
1               5                   10                  15

His Pro Asp Lys Phe Val Gly Ile Thr Tyr Ala Leu Thr
            20                  25

<210> SEQ ID NO 4
<211> LENGTH: 30
<212> TYPE: PRT
<213> ORGANISM: Artificial Sequence
<220> FEATURE:
<223> OTHER INFORMATION: Epitope

<400> SEQUENCE: 4

Ala Val Pro Val Tyr Ile Tyr Phe Asn Thr Trp Thr Thr Cys Gln Ser
1               5                   10                  15

Ile Ala Phe Pro Ser Lys Thr Ser Ala Ser Ile Gly Ser Leu
            20                  25                  30

<210> SEQ ID NO 5
<211> LENGTH: 37
<212> TYPE: PRT
<213> ORGANISM: Artificial Sequence
<220> FEATURE:
<223> OTHER INFORMATION: Epitope

<400> SEQUENCE: 5

Arg Thr Gln Asp Glu Asn Pro Val Val His Phe Phe Lys Asn Ile Val
1               5                   10                  15

Thr Pro Arg Thr Pro Pro Pro Ser Gln Gly Lys Gly Arg Gly Leu Ser
            20                  25                  30

Leu Ser Arg Phe Ser
        35

<210> SEQ ID NO 6
<211> LENGTH: 13
<212> TYPE: PRT
<213> ORGANISM: Artificial Sequence
<220> FEATURE:
<223> OTHER INFORMATION: Epitope

<400> SEQUENCE: 6

His Ser Leu Gly Lys Trp Leu Gly His Pro Asp Lys Phe
1               5                   10

<210> SEQ ID NO 7
<211> LENGTH: 14
<212> TYPE: PRT
<213> ORGANISM: Artificial Sequence
<220> FEATURE:

```
<223> OTHER INFORMATION: Epitope

<400> SEQUENCE: 7

Asn Thr Trp Thr Thr Cys Gln Ser Ile Ala Phe Pro Ser Lys
1               5                   10

<210> SEQ ID NO 8
<211> LENGTH: 21
<212> TYPE: PRT
<213> ORGANISM: Artificial Sequence
<220> FEATURE:
<223> OTHER INFORMATION: Epitope

<400> SEQUENCE: 8

Val His Phe Phe Lys Asn Ile Val Thr Pro Arg Thr Pro Pro Ser
1               5                   10                  15

Gln Gly Lys Gly Arg
            20

<210> SEQ ID NO 9
<211> LENGTH: 22
<212> TYPE: PRT
<213> ORGANISM: Artificial Sequence
<220> FEATURE:
<223> OTHER INFORMATION: Epitope

<400> SEQUENCE: 9

Gln Lys Phe Ser Glu His Phe Ser Ile His Cys Cys Pro Pro Phe Thr
1               5                   10                  15

Phe Leu Asn Ser Lys Arg
            20
```

RNA FOR TREATMENT OF AUTOIMMUNE DISEASES

CROSS REFERENCE TO RELATED PATENT APPLICATIONS

This application claims the benefit of priority under 35 U.S.C. § 371 of International Application No. PCT/EP2018/059188, filed on Apr. 10, 2018, which claims the benefit of priority to International Application No. PCT/EP2017/058651, filed on Apr. 11, 2017. The content of these earlier filed applications is hereby incorporated by reference.

INCORPORATION OF THE SEQUENCE LISTING

The sequence listing submitted herewith as a text file named "37592_0007U1_Sequence_Listing", created on Sep. 19, 2019 and having a size of 4,096 bytes is herein incorporated by reference in its entirety pursuant to 37 C.F.R. § 1.52(e)(5).

The present invention describes non-immunogenic RNA. This RNA forms the basis for the development of therapeutic agents for inducing tolerance towards an autoantigen and thus, for the treatment of autoimmune diseases.

BACKGROUND OF THE INVENTION

The evolution of the immune system resulted in vertebrates in a highly effective network based on two types of defense: the innate and the adaptive immunity. In contrast to the evolutionary ancient innate immune system that relies on invariant receptors recognizing common molecular patterns associated with pathogens, the adoptive immunity is based on highly specific antigen receptors on B cells (B lymphocytes) and T cells (T lymphocytes) and clonal selection. While B cells raise humoral immune responses by secretion of antibodies, T cells mediate cellular immune responses leading to destruction of recognized cells and play a central role in cell-mediated immunity in humans and animals.

Mature T cells recognize and respond to antigen through their antigen-specific receptors (TCR) which interact with immunogenic peptides (epitopes) bound to major histocompatibility complex (MHC) molecules and presented on the surface of target cells. For example, cytotoxic T cells respond to an antigen that is presented in association with MHC-I proteins. Helper T cells recognize antigen presented on MHC-II proteins. The most immediate consequence of TCR activation is the initiation of signaling pathways resulting in clonal expansion of T cells, upregulation of activation markers on the cell surface, differentiation into effector cells, induction of cytotoxicity or cytokine secretion and induction of apoptosis. The TCR is a part of a complex signaling machinery, which includes the heterodimeric complex of the TCR α- and β-chains, the co-receptor CD4 or CD8 and the CD3 signal transduction modul. While the CD3 chains transfer the activation signal inside the cell, the TCR α/β heterodimer is solely responsible for antigen recognition.

In addition to the critical roles that T cells play in the immune response, dendritic cells (DCs) are equally important. DCs are professional antigen-presenting cells having a key regulatory role in the maintenance of tolerance to self-antigens and in the activation of innate and adaptive immunity against foreign antigens.

The immune system can also produce undesirable effects. For example, autoimmune disorders are characterized by the loss of tolerance against autoantigens (self-antigens), activation of lymphocytes reactive against autoantigens, and pathological damage in target organs.

Current therapies for autoimmune disorders mainly concentrate on symptomatic response and on mitigating the immune system as a whole. Antigen-specific therapy has recently emerged as a potential therapy for autoimmune disorders, but eliciting appropriate immune responses has proven difficult and these therapies have met with limited success.

There is thus a need for an effective therapy of autoimmune diseases.

It was the object of the present invention to provide agents for a therapy of autoimmune diseases. This object is achieved according to the invention by the subject matter of the claims.

The present invention encompasses compositions, methods and uses for inducing tolerance to an autoantigen. According to the invention, autoantigens against which an immune response is characteristic of autoimmune diseases are administered in the form of non-immunogenic RNA encoding a peptide or polypeptide comprising the autoantigen or a fragment thereof, or a variant of the autoantigen or fragment. The RNA to be administered in one preferred embodiment is rendered non-immunogenic by incorporating into the RNA modified nucleotides suppressing RNA-mediated activation of innate immune receptors and removing double-stranded RNA (dsRNA). It is demonstrated according to the invention that immunization of mice with non-immunogenic RNA completely blocked any signs of the autoimmune disease. It is demonstrated also that administration of a single disease-driving epitope can be sufficient.

One aspect of the invention relates to a method of treating an autoimmune disease in a subject, comprising administering to the subject non-immunogenic RNA encoding a peptide or polypeptide comprising an autoantigen or a fragment thereof, or a variant of the autoantigen or fragment.

In one embodiment, the autoimmune disease is a T cell-mediated autoimmune disease.

One aspect of the invention relates to a method of inducing tolerance to autoreactive T cells in a subject, comprising administering to the subject non-immunogenic RNA encoding a peptide or polypeptide comprising an autoantigen or a fragment thereof, or a variant of the autoantigen or fragment.

In one embodiment, the subject has an autoimmune disease. In one embodiment, the autoimmune disease is a T cell-mediated autoimmune disease. In one embodiment, the T cells are autoreactive with the autoantigen or cells expressing and preferably presenting the autoantigen.

In one embodiment of the methods of the invention, the autoimmune disease is an autoimmune disease of the CNS. In one embodiment of the methods of the invention, the autoimmune disease is Multiple Sclerosis.

In one embodiment of the methods of the invention, the non-immunogenic RNA when administered does not result in activation of dendritic cells, activation of T cells and/or secretion of IFN-alpha.

In one embodiment of the methods of the invention, the non-immunogenic RNA is rendered non-immunogenic by the incorporation of modified nucleotides and the removal of dsRNA. In one embodiment, the modified nucleotides suppress RNA-mediated activation of innate immune receptors. In one embodiment, the modified nucleotides comprise a replacement of one or more uridines with a nucleoside comprising a modified nucleobase. In one embodiment, the modified nucleobase is a modified uracil. In one embodiment, the nucleoside comprising a modified nucleobase is selected from the group consisting of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnmSU), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-2-thio-uridine (m5 s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethyl-aminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one embodiment, the nucleoside comprising a modified nucleobase is pseudouridine (w), N1-methyl-pseudouridine (m') or 5-methyl-uridine (m⁵U). In one embodiment, the nucleoside comprising a modified nucleobase is 1-methyl-pseudouridine.

In one embodiment of the methods of the invention, the non-immunogenic RNA is mRNA. In one embodiment of the methods of the invention, the non-immunogenic RNA is in vitro transcribed RNA.

In one embodiment of the methods of the invention, the autoantigen is associated with an autoimmune disease. In one embodiment of the methods of the invention, the autoantigen is a T cell-antigen. In one embodiment of the methods of the invention, the autoantigen is CNS-derived. In one embodiment of the methods of the invention, the autoantigen is a myelin antigen. In one embodiment of the methods of the invention, the autoantigen is Myelin Oligodendrocyte Glycoprotein (MOG). In one embodiment of the methods of the invention, the peptide or polypeptide comprising an autoantigen or a fragment thereof, or a variant of the autoantigen or fragment comprises amino acids 35 to 55 of Myelin Oligodendrocyte Glycoprotein (MOG).

In one embodiment of the methods of the invention, the non-immunogenic RNA is transiently expressed in cells of the subject.

In one embodiment of the methods of the invention, the non-immunogenic RNA is delivered to dendritic cells. In one embodiment, the dendritic cells are immature dendritic cells.

In one embodiment of the methods of the invention, the non-immunogenic RNA is formulated in a delivery vehicle. In one embodiment, the delivery vehicle comprises particles. In one embodiment, the delivery vehicle comprises a lipid. In one embodiment, the lipid comprises a cationic lipid. In one embodiment, the lipid forms a complex with and/or encapsulates the non-immunogenic RNA. In one embodiment of the methods of the invention, the non-immunogenic RNA is formulated in liposomes.

One aspect of the invention relates to a pharmaceutical composition comprising non-immunogenic RNA encoding a peptide or polypeptide comprising an autoantigen or a fragment thereof, or a variant of the autoantigen or fragment.

In one embodiment, the non-immunogenic RNA when administered does not result in activation of dendritic cells, activation of T cells and/or secretion of IFN-alpha.

In one embodiment, the non-immunogenic RNA is rendered non-immunogenic by the incorporation of modified nucleotides and the removal of dsRNA. In one embodiment, the modified nucleotides suppress RNA-mediated activation of innate immune receptors. In one embodiment, the modified nucleotides comprise a replacement of one or more uridines with a nucleoside comprising a modified nucleobase. In one embodiment, the modified nucleobase is a modified uracil. In one embodiment, the nucleoside comprising a modified nucleobase is selected from the group consisting of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (Tm5U), 1-taurinomethyl-pseudouridine, 5-taurinomethyl-2-thio-uridine (Tm5s2U), 1-taurinomethyl-4-thio-pseudouridine, 5-methyl-2-thio-uridine (m5s2U), 1-methyl-4-thio-pseudouridine (mis4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one embodiment, the nucleoside comprising a modified nucleobase is pseudouridine (ψ), N1-methyl-pseudouridine (m$^1$ψ) or 5-methyl-uridine (m$^3$U). In one embodiment, the nucleoside comprising a modified nucleobase is 1-methyl-pseudouridine.

In one embodiment of the pharmaceutical composition of the invention, the non-immunogenic RNA is mRNA. In one embodiment of the pharmaceutical composition of the invention, the non-immunogenic RNA is in vitro transcribed RNA.

In one embodiment of the pharmaceutical composition of the invention, the autoantigen is associated with an autoimmune disease. In one embodiment of the pharmaceutical composition of the invention, the autoantigen is a T cell-antigen. In one embodiment of the pharmaceutical composition of the invention, the autoantigen is CNS-derived. In one embodiment of the pharmaceutical composition of the invention, the autoantigen is a myelin antigen. In one embodiment of the pharmaceutical composition of the invention, the autoantigen is Myelin Oligodendrocyte Glycoprotein (MOG). In one embodiment of the pharmaceutical composition of the invention, the peptide or polypeptide comprising an autoantigen or a fragment thereof, or a variant of the autoantigen or fragment comprises amino acids 35 to 55 of Myelin Oligodendrocyte Glycoprotein (MOG).

In one embodiment of the pharmaceutical composition of the invention, the non-immunogenic RNA is transiently expressed in cells of a subject to whom the pharmaceutical composition is administered.

In one embodiment of the pharmaceutical composition of the invention, the non-immunogenic RNA is delivered to dendritic cells of a subject to whom the pharmaceutical composition is administered. In one embodiment, the dendritic cells are immature dendritic cells.

In one embodiment of the pharmaceutical composition of the invention, the non-immunogenic RNA is formulated in a delivery vehicle. In one embodiment, the delivery vehicle comprises particles. In one embodiment, the delivery vehicle comprises a lipid. In one embodiment, the lipid comprises a cationic lipid. In one embodiment, the lipid forms a complex with and/or encapsulates the non-immunogenic RNA. In one embodiment of the pharmaceutical composition of the invention, the non-immunogenic RNA is formulated in liposomes.

One aspect of the invention relates to the pharmaceutical composition of the invention for use in the methods of the invention.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention envisions the treatment or prevention of autoimmune diseases by inducing tolerance of the immune system to an autoantigen associated with the autoimmune disease. Tolerance to the autoantigen is induced by administering non-immunogenic RNA. The non-immunogenic RNA comprises sequences encoding a peptide or polypeptide comprising the autoantigen or a fragment thereof, or a variant of the autoantigen or fragment that suppresses an immune response to said autoantigen when administered to a subject.

In various embodiments, the non-immunogenic RNA described herein has a length of between 200 to 20000 nucleotides, 500 to 5000 nucleotides, 500 to 2500 nucleotides, in particular 600 to 2500 nucleotides or 800 to 2000 nucleotides.

According to the invention it is preferred to administer the non-immunogenic RNA described herein formulated in carriers or delivery vehicles such as in a nanoparticulate formulation, in particular a lipoplex formulation. Accordingly, the non-immunogenic RNA molecules described herein may be present formulated in carriers or delivery vehicles such as in nanoparticulates or a nanoparticulate formulation, in particular a lipoplex formulation, as described herein.

In one embodiment, delivery vehicles may be used which deliver the non-immunogenic RNA molecules to antigen presenting cells such as dendritc cells (DCs) in the spleen after systemic administration. For example, nanoparticulate RNA formulations with defined particle size wherein the net charge of the particles is close to zero or negative, such as electro-neutral or negatively charged lipoplexes from RNA and liposomes, e.g. lipoplexes comprising DOTMA and DOPE or DOTMA and Cholesterol, lead to substantial delivery of RNA to spleen DCs after systemic administration. Particularly preferred according to the invention is a nanoparticulate RNA formulation wherein the charge ratio of positive charges to negative charges in the nanoparticles is 1.4:1 or less and/or the zeta potential of the nanoparticles is 0 or less. In one embodiment, the charge ratio of positive charges to negative charges in the nanoparticles is between 1.4:1 and 1:8, preferably between 1.2:1 and 1:4, e.g. between 1:1 and 1:3 such as between 1:1.2 and 1:2, 1:1.2 and 1:1.8, 1:1.3 and 1:1.7, in particular between 1:1.4 and 1:1.6, such as about 1:1.5. In one embodiment, the zeta potential of the nanoparticles is −5 or less, −10 or less, −15 or less, −20 or less or −25 or less. In various embodiments, the zeta potential of the nanoparticles is −35 or higher, −30 or higher or −25 or higher. In one embodiment, the nanoparticles have a zeta potential from 0 mV to −50 mV, preferably 0 mV to −40 mV or −10 mV to −30 mV. In one embodiment, the positive charges are contributed by at least one cationic lipid present in the nanoparticles and the negative charges are contributed by the RNA. In one embodiment, the nanoparticles comprises at least one helper lipid. The helper lipid may be a neutral or an anionic lipid.

In one embodiment, the nanoparticles are lipoplexes comprising DOTMA and DOPE in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTMA and Cholesterol in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTAP and DOPE in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTMA and DOPE in a molar ratio of 2:1 to 1:2, preferably 2:1 to 1:1, and wherein the charge ratio of positive charges in DOTMA to negative charges in the RNA is 1.4:1 or less.

In one embodiment, the nanoparticles are lipoplexes comprising DOTMA and cholesterol in a molar ratio of 2:1 to 1:2, preferably 2:1 to 1:1, and wherein the charge ratio of positive charges in DOTMA to negative charges in the RNA is 1.4:1 or less.

In one embodiment, the nanoparticles are lipoplexes comprising DOTAP and DOPE in a molar ratio of 2:1 to 1:2, preferably 2:1 to 1:1, and wherein the charge ratio of positive charges in DOTAP to negative charges in the RNA is 1.4:1 or less.

In one embodiment, the non-immunogenic RNA according to the invention is formulated in F12 or F5 liposomes, preferably F12 liposomes.

According to the invention, the term "F12" designates liposomes comprising DOTMA and DOPE in a molar ratio of 2:1 and lipoplexes with RNA which are formed using such liposomes.

According to the invention, the term "F5" designates liposomes comprising DOTMA and cholesterol in a molar ratio of 1:1 and lipoplexes with RNA which are formed using such liposomes.

As used herein, the term "nanoparticle" refers to any particle having a diameter making the particle suitable for systemic, in particular parenteral, administration, of, in particular, nucleic acids, typically a diameter of less than 1000 nanometers (nm). In some embodiments, a nanoparticle has a diameter of less than 600 nm. In some embodiments, a nanoparticle has a diameter of less than 400 nm. In some embodiments, a nanoparticle has an average diameter in the range of from about 50 nm to about 1000 nm, preferably from about 50 nm to about 400 nm, preferably about 100 nm to about 300 nm such as about 150 nm to about 200 nm. In some embodiments, a nanoparticle has a diameter in the range of about 200 to about 700 nm, about 200 to about 600 nm, preferably about 250 to about 550 nm, in particular about 300 to about 500 nm or about 200 to about 400 nm.

As used herein, the term "nanoparticulate formulation" or similar terms refer to any 30 substance that contains at least one nanoparticle. In some embodiments, a nanoparticulate formulation is a uniform collection of nanoparticles. In some embodiments, nanoparticulate formulations are dispersions or emulsions. In general, a dispersion or emulsion is formed when at least two immiscible materials are combined.

The term, "lipoplex" or "nucleic acid lipoplex", in particular "RNA lipoplex", refers to a complex of lipids and nucleic acids, in particular RNA. Lipoplexes are formed spontaneously when cationic liposomes, which often also include a neutral "helper" lipid, are mixed with nucleic acids.

If the present invention refers to a charge such as a positive charge, negative charge or neutral charge or a cationic compound, negative compound or neutral compound this generally means that the charge mentioned is present at a selected pH, such as a physiological pH. For example, the term "cationic lipid" means a lipid having a net positive charge at a selected pH, such as a physiological pH. The term "neutral lipid" means a lipid having no net positive or negative charge and can be present in the form of a non-charge or a neutral amphoteric ion at a selected pH, such as a physiological pH. By "physiological pH" herein is meant a pH of about 7.5.

The nanoparticulate carriers such as lipid carriers contemplated for use in the present invention include any substances or vehicles with which nucleic acid such as RNA can be associated, e.g. by forming complexes with the nucleic acid or forming vesicles in which the nucleic acid is enclosed or encapsulated. This may result in increased stability of the nucleic acid compared to naked nucleic acid. In particular, stability of the nucleic acid in blood may be increased.

Cationic lipids, cationic polymers and other substances with positive charges may form complexes with negatively charged nucleic acids. These cationic molecules can be used to complex nucleic acids, thereby forming e.g. so-called lipoplexes or polyplexes, respectively, and these complexes have been shown to deliver nucleic acids into cells.

Nanoparticulate nucleic acid preparations for use in the present invention can be obtained by various protocols and from various nucleic acid complexing compounds. Lipids, polymers, oligomers, or amnphiphiles are typical complexing agents. In one embodiment, the complexing compound comprises at least one agent selected from the group consisting protamine, polyethyleneimine, a poly-L-lysine, a poly-L-arginine or a histone.

According to the invention, protamine is useful as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in along-acting formulation of insulin and to neutralize the anticoagulant effects of heparin. According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources. The protamine used according to the present invention can be sulfated protamine or hydrochloride protamine. In a preferred embodiment, the protamine source used for the production of the nanoparticles described herein is protamine 5000 which contains protamine at more than 10 mg/ml (5000 heparin-neutralizing units per ml) in an isotonic salt solution.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. The described phases may be present in the nanoparticulate nucleic acid formulations of the present invention.

For formation of nucleic acid lipoplexes from nucleic acid and liposomes, any suitable method of forming liposomes can be used so long as it provides the envisaged nucleic acid lipoplexes. Liposomes may be formed using standard methods such as the reverse evaporation method (REV), the ethanol injection method, the dehydration-rehydration method (DRV), sonication or other suitable methods.

After liposome formation, the liposomes can be sized to obtain a population of liposomes having a substantially homogeneous size range.

Bilayer-forming lipids have typically two hydrocarbon chains, particularly acyl chains, and a head group, either polar or nonpolar. Bilayer-forming lipids are either composed of naturally-occurring lipids or of synthetic origin, including the phospholipids, such as phosphatidylcholine, phosphatidylethanolamine, phosphatide acid, phosphatidylinositol, and sphingomyelin, where the two hydrocarbon chains are typically between about 14-22 carbon atoms in length, and have varying degrees of unsaturation. Other suitable lipids for use in the composition of the present invention include glycolipids and sterols such as cholesterol and its various analogs which can also be used in the liposomes.

Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Preferred are DOTMA, DOTAP, DODAC, and DOSPA. Most preferred is DOTMA.

In addition, the nanoparticles described herein preferably further include a neutral lipid in view of structural stability and the like. The neutral lipid can be appropriately selected in view of the delivery efficiency of the nucleic acid-lipid complex. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, sterol, and cerebroside. Preferred is DOPE and/or DOPC. Most preferred is DOPE. In the case where a cationic liposome includes both a cationic lipid and a neutral lipid, the molar ratio of the cationic lipid to the neutral lipid can be appropriately determined in view of stability of the liposome and the like.

According to one embodiment, the nanoparticles described herein may comprise phospholipids. The phospholipids may be a glycerophospholipid. Examples of glycerophospholipid include, without being limited thereto, three types of lipids: (i) zwitterionic phospholipids, which include, for example, phosphatidylcholine (PC), egg yolk phosphatidylcholine, soybean-derived PC in natural, partially hydrogenated or fully hydrogenated form, dimyristoyl phosphatidylcholine (DMPC) sphingomyelin (SM); (ii) negatively charged phospholipids: which include, for example, phosphatidylserine (PS), phosphatidylinositol (PI), phosphatidic acid (PA), phosphatidylglycerol (PG) dipalmipoyl PG, dimyristoyl phosphatidylglycerol (DMPG); synthetic derivatives in which the conjugate renders a zwitterionic phospholipid negatively charged such is the case of methoxy-polyethylene,glycol-distearoyl phosphatidylethanolamine (mPEG-DSPE); and (iii) cationic phospholipids, which include, for example, phosphatidylcholine or sphingomyelin of which the phosphomonoester was O-methylated to form the cationic lipids.

Association of nucleic acid to the lipid carrier can occur, for example, by the nucleic acid filling interstitial spaces of the carrier, such that the carrier physically entraps the nucleic acid, or by covalent, ionic, or hydrogen bonding, or by means of adsorption by non-specific bonds.

The term "immune response" relates to a reaction of the immune system, preferably to an antigen, and preferably refers to a cellular immune response, a humoral immune response, or both. According to the invention, the term "immune response to" or "immune response against" with respect to a target such as an antigen, cell or tissue, relates to an immune response directed against the target.

The immune system is divided into two parts, the innate and adaptive systems. The adaptive immune response depends on B and T lymphocytes which are specific for particular antigens. The innate immune system responds to common structures shared by a vast majority of threats. These common structures are called pathogen associated molecular patterns, or PAMPs, and are recognized by the toll-like receptors, or TLRs.

In addition to the cellular TLRs, an important part of the innate immune system is the humoral complement system that opsonizes and kills pathogens through the PAMP recognition mechanism. These highly conserved soluble and membrane bound proteins are collectively called Pattern-Recognition Receptors (PRRs), and it is the PAMP/PRR interaction that triggers the innate immune system.

TLRs are transmembrane proteins expressed by cells of the innate immune system, which recognize invading microbes and activate signaling pathways that launch immune and inflammatory responses to destroy the invaders. Different TLRs serve as receptors for diverse ligands, including bacterial cell wall components, viral double-stranded RNA and small-molecule anti-viral or immunomodulatory compounds. In humans, TLR3, 7, 8 and 9 respond primarily to nucleic acid based PAMPs from viruses and bacteria.

The terms "cellular immune response", "cellular response", "cell-mediated immunity" or similar terms are meant to include a cellular response directed to cells characterized by expression of an antigen and/or presentation of an antigen with class I or class II MHC. The cellular response relates to cells called T cells or T lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill cells such as diseased cells.

The term "humoral immune response" refers to a process in living organisms wherein antibodies are produced in response to agents and organisms, which they ultimately neutralize and/or eliminate. The specificity of the antibody response is mediated by T and/or B cells through membrane-associated receptors that bind antigen of a single specificity. Following binding of an appropriate antigen and receipt of various other activating signals, B lymphocytes divide, which produces memory B cells as well as antibody secreting plasma cell clones, each producing antibodies that recognize the identical antigenic epitope as was recognized by its antigen receptor. Memory B lymphocytes remain dormant until they are subsequently activated by their specific antigen. These lymphocytes provide the cellular basis of memory and the resulting escalation in antibody response when re-exposed to a specific antigen.

The term "antibody" as used herein, refers to an immunoglobulin molecule, which is able to specifically bind to an epitope on an antigen. In particular, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3, the CDRs of a VL are termed LCDR1, LCDR2 and LCDR3. The variable regions of the heavy and light chains contain a binding domain that interacts with an antigen. The constant regions of an antibody comprise the heavy chain constant region (CH) and the light chain constant region (CL), wherein CH can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and the first component (Clq) of the classical complement system. Antibodies can be intact immunoglobulins derived from natural sources or from recombinant sources and can be immunoactive portions of intact immunoglobulins. Antibodies are typically tetramers of immunoglobulin molecules. Antibodies may exist in a variety of forms including, for example, polyclonal antibodies, monoclonal antibodies, Fv, Fab and F(ab)2, as well as single chain antibodies and humanized antibodies.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the VL (variable light chain) domain, CL (constant light chain) domain, $V_H$ (variable heavy chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

According to the invention, the term "antigen" or "immunogen" covers any substance, preferably a peptide or protein, that is a target of an immune response and/or that will elicit an immune response. In particular, an "antigen" relates to any substance that reacts specifically with antibodies or T-lymphocytes (T-cells).

According to the present invention, the term "antigen" comprises any molecule which comprises at least one epitope such as a B cell or T cell epitope. Preferably, an antigen in the context of the present invention is a molecule which, optionally after processing, induces an immune reaction, which is preferably specific for the antigen or cells expressing the antigen. Antigens may include or may be derived from allergens, viruses, bacteria, fungi, parasites and other infectious agents and pathogens or an antigen may also be a tumor antigen.

A "self-antigen" or "autoantigen" is an antigen derived from an organism which under normal circumstances is not recognized by the immune system of that organism, but which may become a target of immune attack, resulting in an autoimmune disease.

In a preferred embodiment, an autoantigen is associated with an autoimmune disease.

The term "autoantigen associated with an autoimmune disease" refers to an autoantigen that is of pathological significance for an autoimmune disease. In one embodiment, an autoantigen associated with an autoimmune disease is a molecule which contains at least one epitope against which an immune reaction is directed in a patient having an autoimmune disease.

A peptide or polypeptide comprising an autoantigen or a fragment thereof, or a variant of the autoantigen or fragment which is provided according to the invention to a subject by administering non-immunogenic RNA coding for the peptide or polypeptide should result in a reduced immune response to the autoantigen. Thus, a peptide or polypeptide comprising an autoantigen or a fragment thereof, or a variant of the autoantigen or fragment provided according to the invention may correspond to or comprise an autoantigen associated with an autoimmune disease, or a variant thereof (including fragments of the autoantigen and variants thereof). In one embodiment, such fragments or variants are immunologically equivalent to an autoantigen associated with an autoimmune disease in that—similar to the autoantigen—their provision results in tolerance to autoreactive T cells targeting the autoantigen or cells expressing the autoantigen and optionally presenting the autoantigen in the context of MHC molecules. Thus, a peptide or polypeptide comprising an autoantigen or a fragment thereof, or a variant of the autoantigen or fragment provided according to the invention may be identical to an autoantigen associated with an autoimmune disease, may comprise an autoantigen associated with an autoimmune disease or a portion or fragment thereof or may comprise an antigen which is homologous to an autoantigen associated with an autoimmune disease or a portion or fragment thereof.

If a peptide or polypeptide comprising an autoantigen or a fragment thereof, or a variant of the autoantigen or fragment provided according to the invention comprises a portion or fragment of the autoantigen associated with an autoimmune disease or a portion or fragment of an antigen which is homologous to an autoantigen associated with an autoimmune disease said portion or fragment may comprise an epitope of the autoantigen associated with an autoimmune disease, in particular an epitope of the autoantigen associated with an autoimmune disease to which autoreactive T cells are targeted. Thus, according to the invention, a peptide or polypeptide comprising an autoantigen or a fragment thereof, or a variant of the autoantigen or fragment may comprise an immunogenic fragment of an autoantigen associated with an autoimmune disease such as a peptide fragment of an autoantigen associated with an autoimmune disease. An "immunogenic fragment of an autoantigen" according to the invention preferably relates to a portion or fragment of an autoantigen which is capable of stimulating a T cell response. Said portion or fragment when provided according to the invention may also be capable of inducing tolerance to autoreactive T cells. A peptide or polypeptide comprising an autoantigen or a fragment thereof, or a variant of the autoantigen or fragment provided according to the invention may be a recombinant peptide or polypeptide and/or non-immunogenic RNA coding therefor according to the invention may be recombinant RNA.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present invention, the term "immunologically equivalent" is preferably used with respect to the immunological effects or properties of antigens or antigen variants.

In one embodiment of the invention, a peptide or polypeptide provided according to the invention by administering non-immunogenic RNA comprises at least one epitope from an autoantigen, which preferably is an autoantigen recognized in an autoimmune disease condition, such as an autoimmune disease condition described herein. In one embodiment, a peptide or polypeptide provided according to the invention comprises an epitope to which a subject is self-reactive.

The term "epitope" refers to an antigenic determinant in a molecule such as an antigen, i.e., to a part in or fragment of the molecule that is recognized, i.e. bound, by the immune system, for example, that is recognized by an antibody or T cell receptor. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Preferably, the term relates to an immunogenic portion of an antigen comprising the epitope. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is preferred that the epitope in the context of the present invention is a T cell epitope.

As used herein, the term "T cell epitope" refers to a peptide which binds to a MHC molecule in a configuration recognized by a T cell receptor. Typically, T cell epitopes are presented on the surface of an antigen presenting cell. Preferably, T cell epitopes are MHC class I and/or class II presented peptides. Preferably, T cell epitopes comprise an amino acid sequence substantially corresponding to the amino acid sequence of a fragment of an antigen. Preferably, said fragment of an antigen is an MHC class I and/or class II presented peptide. A peptide which is suitable for binding to an MHC molecule, in particular a class I MHC molecule, preferably is 7-20 amino acids in length, more preferably 7-12 amino acids in length, more preferably 8-11 amino acids in length, in particular 9 or 10 amino acids in length. In one embodiment, a T cell epitope when presented in the context of MHC such as MHC of antigen presenting cells is recognized by a T cell receptor. The T cell epitope if recognized by a T cell receptor may be able to induce in the presence of appropriate co-stimulatory signals, clonal expansion of the T cell carrying the T cell receptor specifically recognizing the T cell epitope.

According to the invention, an epitope such as a T cell epitope of an autoantigen may be present in a peptide or polypeptide provided according to the invention by administering non-immunogenic RNA as a part of a larger entity such as a sequence comprising more of an autoantigen than just the epitope and/or a polypeptide comprising more than one epitope of either one or more than one autoantigens. The presented peptide or T cell epitope is produced following suitable processing. Also, T cell epitopes may be modified at one or more residues that are not essential for TCR recognition or for binding to MHC. Such modified T cell epitopes may be considered immunologically equivalent.

The non-immunogenic RNA described herein can be customized for various diseases requiring immune tolerance such as autoimmune diseases and can also be customized for individual patients. Various immunoassays exist to determine whether immune cells circulating in the blood in a given patient develop an immune response to particular peptides tested. Alternatively, the antigens or epitopes selected can be based on the most common reactivity seen in a class of patients.

"Cell surface" is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells. In one embodiment, an antigen expressed on the surface of cells is an integral membrane protein having an extracellular portion.

The term "extracellular portion" or "exodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The terms "portion" or "part" are used interchangeably herein and refer to a continuous or discontinuous element of a structure such as an amino acid sequence.

The term "fragment" refers to a continuous element of a structure such as an amino acid sequence. A portion, part or fragment of a structure preferably comprises one or more functional properties, e.g. antigenic, immunologic and/or binding properties, of said structure. A portion or part of a protein sequence preferably comprises at least 6, in particular at least 8, at least 12, at least 15, at least 20, at least 30, at least 50, or at least 100 consecutive and/or non-consecutive amino acids of the protein sequence. A fragment of a protein sequence preferably comprises at least 6, in particular at least 8, at least 12, at least 15, at least 20, at least 30, at least 50, or at least 100 consecutive amino acids of the protein sequence.

The term "immunogenicity" relates to the relative effectivity of an antigen to induce an immune reaction.

The term "immunostimulatory" is used herein to refer to increasing overall immune response.

"Immune tolerance", "immunological tolerance", or simply "tolerance" describes a state of unresponsiveness of the immune system to substances or tissue that have the capacity to elicit an immune response. Immune tolerance, which prevents an immunogenic response from developing upon self-recognition, is mediated by several mechanisms, primarily involving the presentation of "self" peptides to CD4+ or CD8+ T cells in a manner that results in the elimination, inhibition, or conversion of the autoreactive T cells that otherwise would potentially attack cells and tissues that are the source of autoantigens and/or support the production by B cells of antibodies that react against these autoantigens. The mechanisms by which tolerance is established are distinct, but the resulting effect is similar. Insufficient induction of tolerance to self-antigens from particular tissues is the major cause for tissue-specific autoimmune diseases. Under normal conditions, tissue-specific self-antigens are presented by tolerance-inducing (tolerogenic) cells, which program any reactive T cells to undergo cell death, unresponsiveness or conversion to a type of Treg. In autoimmune diseases, these same self-antigens are either not presented sufficiently, which limit engagement of autoreactive T cells for instruction, or presented improperly, instructing specific T cells to mount an immune response instead of tolerating the antigen as self. Antigen-specific therapies that deliver these self-antigens to potent tolerogenic cells, systematically or via the mucosa are partially able to reinstate tolerance in part through the generation of suppressor T cells able to counteract improperly activated pathogenic T cells.

The term "target" shall mean an agent such as a cell, which is a target for an immune response. Targets include cells that present an antigen or an antigen epitope, i.e. a peptide fragment derived from an antigen through antigen processing.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells. An antigen presenting cell includes, but is not limited to, monocytes/macrophages, B cells and dendritic cells (DCs). According to the invention, the term "antigen-presenting cell" includes professional antigen-presenting cells and non-professional antigen-presenting cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

By "cell characterized by presentation of an antigen" or "cell presenting an antigen" or similar expressions is meant a cell such as an antigen presenting cell presenting an antigen or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC.

The term "immunoreactive cell" or "effector cell" in the context of the present invention relates to a cell which exerts effector functions during an immune reaction. An "immunoreactive cell" preferably is capable of binding an antigen or a cell characterized by expression and/or presentation of an antigen or an epitope and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells.

Preferably, an "immunoreactive cell" recognizes an antigen or an epitope with some degree of specificity, in particular if presented in the context of MHC molecules such as on the surface of antigen presenting cells. Preferably, said recognition enables the cell that recognizes an antigen or an epitope to be responsive or reactive. If the cell is a helper T cell ($CD4^+$ T cell) bearing receptors that recognize an antigen or an epitope in the context of MHC class II molecules such responsiveness or reactivity may involve the release of cytokines and/or the activation of $CD8^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an epitope and are responsive or reactive are also termed "antigen-responsive CTL" herein. If the cell is a B cell such responsiveness may involve the release of immunoglobulins.

The term "T cell" or "T lymphocyte" relates to thymus-derived cells that participate in a variety of cell-mediated immune reactions and includes T helper cells ($CD4^+$ T cells) and cytotoxic T cells (CTLs, $CD8^+$ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as $CD4^+$ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens. The constant domain of the TCR domain consists of short connecting sequences in which a cysteine residue forms disulfide bonds, which forms a link between the two chains.

The term "B cell" or "B lymphocyte" relates to a type of white blood cell of the lymphocyte subtype which function in humoral immunity by secreting antibodies. Additionally, B cells present antigen and are classified as professional antigen-presenting cells (APCs) and secrete cytokines. B cells express B cell receptors (BCRs) on their cell membrane. BCRs allow the B cell to bind a specific antigen, against which it will initiate an antibody response. The B-cell receptor is composed of two parts, a membrane-bound immunoglobulin molecule of one isotype (IgD, IgM, IgA, IgG, or IgE) which with the exception of the presence of an integral membrane domain are identical to their secreted forms and a signal transduction moiety: a heterodimer called Ig-α/Ig-β (CD79), bound together by disulfide bridges. Each member of the dimer spans the plasma membrane and has a cytoplasmic tail bearing an immunoreceptor tyrosine-based activation motif (ITAM).

B cell activation occurs in the secondary lymphoid organs, such as the spleen and lymph nodes. After B cells mature in the bone marrow, they migrate through the blood to secondary lymphoid organs, which receive a constant supply of antigen through circulating lymph. B cell activation begins when the B cell binds to an antigen via its BCR. Different B cell subsets undergo T cell-dependent activation or T cell-independent activation.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self-antigens (peptide fragments from the cell itself) and nonself-antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and f-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

The term "immune effector functions" or "effector functions" in the context of the present invention includes any functions mediated by components of the immune system that result, for example, in the killing of cells. Preferably, the immune effector functions in the context of the present invention are T cell mediated effector functions. Such functions comprise in the case of a helper T cell ($CD4^+$ T cell) the recognition of an antigen or an antigen peptide derived from an antigen in the context of MHC class II molecules by T cell receptors, the release of cytokines and/or the activation of $CD8^+$ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

The term "toll-like receptor" or "TLR" relates to a class of proteins that play a key role in the innate immune system. They are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses.

In one embodiment of the invention, non-immunogenic RNA that codes for a peptide or polypeptide comprising an autoantigen or a fragment thereof, or a variant of the autoantigen or fragment is administered to a subject. A translation product of the RNA may be formed in cells of the subject and the product may be displayed to the immune system for inducing tolerance to autoreactive T cells targeting the autoantigen.

Alternatively, the present invention envisions embodiments wherein non non-immunogenic RNA expressing a peptide or polypeptide comprising an autoantigen or a fragment thereof, or a variant of the autoantigen or fragment is introduced into cells such as antigen-presenting cells ex vivo, e.g. antigen-presenting cells taken from a patient, and the cells, optionally clonally propagated ex vivo, are transplanted back into the same patient. Transfected cells may be reintroduced into the patient using any means known in the art, preferably in sterile form by intravenous, intracavitary, or intraperitoneal administration. Suitable cells include antigen-presenting cells. The antigen presenting cell preferably is a dendritic cell, a macrophage, a B cell, a mesenchymal stromal cell, an epithelial cell, an endothelial cell and a fibroblastic cell, and most preferably is a dendritic cell. Thus, the invention also include a method for treating an autoimmune disease, comprising administering to a subject in need isolated antigen-presenting cells that expresses the non-immunogenic RNA described herein. The cells may be autologous, allogeneic, syngeneic or heterologous to the subject.

The term "nucleic acid", as used herein, is intended to include deoxyribonucleic acid (DNA) or ribonucleic acid (RNA) such as cDNA, mRNA, recombinantly produced and chemically synthesized molecules. A nucleic acid may be single-stranded or double-stranded. According to the invention, RNA includes in vitro transcribed RNA (IVT RNA) or synthetic RNA. According to the invention, a nucleic acid is preferably an isolated nucleic acid. Furthermore, the nucleic acids described herein may be recombinant molecules.

The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally-occurring DNA.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially or completely purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA. According to the present invention, the term "RNA" includes and preferably relates to "mRNA" which means "messenger RNA" and relates to a transcript which may be produced using DNA as template and encodes a peptide or protein. mRNA typically comprises a 5' non translated region (5'-UTR), a protein or peptide coding region and a 3' non translated region (3'-UTR). mRNA has a limited halftime in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The RNA to be administered according to the invention is non-immunogenic. The term "non-immunogenic RNA" as used herein refers to RNA that does not induce a response by the immune system upon administration, e.g., to a mammal, or induces a weaker response than would have been induced by the same RNA that differs only in that it has not been subjected to the modifications and treatments that render the non-immunogenic RNA non-immunogenic. In one preferred embodiment non-immunogenic RNA is rendered non-immunogenic by incorporating modified nucleotides suppressing RNA-mediated activation of innate immune receptors into the RNA and removing double-stranded RNA (dsRNA).

For rendering the non-immunogenic RNA non-immunogenic by the incorporation of modified nucleotides, any modified nucleotide may be used as long as it lowers or suppresses immunogenicity of the RNA. Particularly preferred are modified nucleotides that suppress RNA-mediated activation of innate immune receptors. In one embodiment, the modified nucleotides comprises a replacement of one or more uridines with a nucleoside comprising a modified nucleobase. In one embodiment, the modified nucleobase is a modified uracil. In one embodiment, the nucleoside comprising a modified nucleobase is selected from the group consisting of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (Wm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one particularly preferred embodiment, the nucleoside comprising a modified nucleobase is pseudouridine (ψ), N1-methyl-pseudouridine (m1ψ) or 5-methyl-uridine (m5U), in particular 1-methyl-pseudouridine.

The structure of an exemplary nucleoside comprising a modified nucleobase is 1-methylpseudouridine m1ψ:

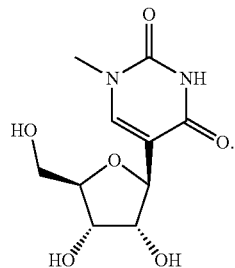 [SMILES: Cn1cc([C@@H]2O[C@H](CO)[C@@H](O)[C@H]2O)c(=O)[nH]c1=O]

In one embodiment, the replacement of one or more uridines with a nucleoside comprising a modified nucleobase comprises a replacement of at least 1%, at least 2%, at least 3%, at least 4%, at least 5%, at least 10%, at least 25%, at least 50%, at least 75%, at least 90%, at least 95%, at least 96%, at least 97%, at least 98%, at least 99% or 100% of the uridines.

During synthesis of mRNA by in vitro transcription (IVT) using T7 RNA polymerase significant amounts of aberrant products, including double-stranded RNA (dsRNA) are produced due to unconventional activity of the enzyme. dsRNA induces inflammatory cytokines and activates effector enzymes leading to protein synthesis inhibition. dsRNA can be removed from RNA such as IVT RNA, for example, by ion-pair reversed phase HPLC using a non-porous or porous C-18 polystyrene-divinylbenzene (PS-DVB) matrix. Alternatively, an enzymatic based method using *E. coli* RNaseIII that specifically hydrolyzes dsRNA but not ssRNA, thereby eliminating dsRNA contaminants from IVT RNA preparations can be used. Furthermore, dsRNA can be separated from ssRNA by using a cellulose material. In one embodiment, an RNA preparation is contacted with a cellulose material and the ssRNA is separated from the cellulose material under conditions which allow binding of dsRNA to the cellulose material and do not allow binding of ssRNA to the cellulose material.

As the term is used herein, "remove" or "removal" refers to the characteristic of a population of first substances, such as non-immunogenic RNA, being separated from the proximity of a population of second substances, such as dsRNA, wherein the population of first substances is not necessarily devoid of the second substance, and the population of second substances is not necessarily devoid of the first substance. However, a population of first substances characterized by the removal of a population of second substances has a measurably lower content of second substances as compared to the non-separated mixture of first and second substances.

Nucleic acids can be transferred into a host cell by physical, chemical or biological means.

Physical methods for introducing a nucleic acid into a host cell include calcium phosphate precipitation, lipofection, particle bombardment, microinjection, electroporation, and the like.

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

"Encoding" refers to the inherent property of specific sequences of nucleotides in a nucleic acid to serve as templates for synthesis of other polymers and macromolecules in biological processes having either a defined sequence of nucleotides or a defined sequence of amino acids. Thus, a nucleic acid encodes a protein if expression (translation and optionally transcription) of the nucleic acid produces the protein in a cell or other biological system.

The term "expression" is used according to the invention in its most general meaning and comprises the production of RNA and/or peptides or polypeptides, e.g. by transcription and/or translation. With respect to RNA, the term "expression" or "translation" relates in particular to the production of peptides or polypeptides. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a 17 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide or polypeptide.

According to the invention it is preferred that a nucleic acid such as RNA encoding a peptide or protein once taken up by or introduced, i.e. transfected or transduced, into a cell which cell may be present in vitro or in a subject results in expression of said peptide or protein. The cell may express the encoded peptide or protein intracellularly (e.g. in the cytoplasm and/or in the nucleus), may secrete the encoded peptide or protein, or may express it on the surface.

According to the invention, terms such as "nucleic acid expressing" and "nucleic acid encoding" or similar terms are used interchangeably herein and with respect to a particular peptide or polypeptide mean that the nucleic acid, if present in the appropriate environment, preferably within a cell, can be expressed to produce said peptide or polypeptide.

Terms such as "transferring", "introducing", "transfecting" or "transducing" are used interchangeably herein and relate to the introduction of nucleic acids, in particular exogenous or heterologous nucleic acids, such as RNA into a cell. According to the present invention, the cell can be present in vitro or in vivo, e.g. the cell can form part of an organ, a tissue and/or an organism. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cell lines allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, the term "peptide" refers to substances comprising two or more, preferably 3 or more, preferably 4 or more, preferably 6 or more, preferably 8 or more, preferably 10 or more, preferably 13 or more, preferably 16 or more, preferably 21 or more and up to preferably 8, 10, 20, 30, 40 or 50, in particular 100 amino acids joined covalently by peptide bonds.

The term "protein" refers to large peptides, i.e. polypeptides, preferably to peptides with more than 100 amino acid residues, but in general the terms "peptide", "polypeptide" and "protein" are synonyms and are used interchangeably herein.

The present invention also includes "variants" of the peptides, proteins, or amino acid sequences such as autoantigens described herein.

For the purposes of the present invention, "variants" of an amino acid sequence comprise amino acid insertion variants, amino acid addition variants, amino acid deletion variants and/or amino acid substitution variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids.

A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. The degree of similarity or identity is given preferably for a segment of at least 80, at least 100, at least 120, at least 150, at least 180, at least 200 or at least 250 amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "% identity" is intended to refer, in particular, to a percentage of amino acid residues which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

According to the invention, a variant, fragment, part or portion of an amino acid sequence, peptide or protein preferably has a functional property of the amino acid sequence, peptide or protein, respectively, from which it has been derived, i.e. it is functionally equivalent. In one embodiment, a variant, fragment, part or portion of an amino acid sequence, peptide or protein is immunologically equivalent to the amino acid sequence, peptide or protein, respectively, from which it has been derived. In one embodiment, the functional property is an immunological property.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

The term "derived" means according to the invention that a particular entity, in particular a particular sequence, is present in the object from which it is derived, in particular an organism or molecule. In the case of amino acid or nucleic acid sequences, especially particular sequence regions, "derived" in particular means that the relevant amino acid sequence or nucleic acid sequence is derived from an amino acid sequence or nucleic acid sequence in which it is present.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., E. coli) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines.

A cell which comprises a nucleic acid, e.g. which has been transfected with a nucleic acid, preferably expresses the peptide or protein encoded by the nucleic acid.

The term "expansion" refers to a process wherein a specific entity is multiplied. In one embodiment of the present invention, the term is used in the context of an immunological response in which lymphocytes are stimulated by an antigen, proliferate, and the specific lymphocyte recognizing said antigen is amplified. Preferably, clonal expansion leads to differentiation of the lymphocytes.

"Isolated" as used herein, is intended to refer to a molecule which is substantially free of other molecules such as other cellular material.

The term "recombinant" in the context of the present invention means "made through genetic engineering". Preferably, a "recombinant object" such as a recombinant cell or nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

Terms such as "reducing", "inhibiting" or "decreasing" relate to the ability to cause an overall decrease, preferably of 5% or greater, 10% or greater, 20% or greater, more preferably of 50% or greater, and most preferably of 75% or greater, in the level. These terms include a complete or essentially complete inhibition, i.e. a reduction to zero or essentially to zero.

Terms such as "increasing", "enhancing", "promoting", "stimulating", or "inducing" relate to the ability to cause an overall increase, preferably of 5% or greater, 10% or greater, 20% or greater, 50% or greater, 75% or greater, 100% or greater, 200% or greater, or 500% or greater, in the level. These terms may relate to an increase, enhancement, promotion, stimulation, or inducement from zero or a non-measurable or non-detectable level to a level of more than zero or a level which is measurable or detectable. Alternatively, these terms may also mean that there was a certain level before an increase, enhancement, promotion, stimulation, or inducement and after the increase, enhancement, promotion, stimulation, or inducement the level is higher.

The agents and compositions described herein are useful in methods of suppressing an immune response in a mammal for the treatment or prevention of an autoimmune disease. In particular, the agents and compositions described herein can be used to treat a subject with an autoimmune disease characterized by the presence of an immune reaction against an autoantigen. According to the invention non-immunogenic RNA encoding a peptide or polypeptide comprising the autoantigen or a fragment thereof, or a variant of the autoantigen or fragment is administered to the subject.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes autoimmune diseases.

A disease to be treated according to the invention is preferably a disease involving an autoantigen or being associated with an autoantigen.

The term "autoimmune disease" or "autoimmune disorder" refers to any disease/disorder in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Examples of autoimmune diseases include, but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, and type I diabetes mellitus, among others.

Below is a list of antigens that are known to be associated with certain autoimmune diseases. Epitopes from these antigens can be included in a peptide or polypeptide comprising an autoantigen or a fragment thereof, or a variant of the autoantigen or fragment according to the invention.

Multiple Sclerosis (MS)/(+ Animal Model EAE (Experimental Autoimmune Encephalomyelitis))

Possible candidate autoantigens in MS include myelin antigens, neuronal antigens and astrocyte-derived antigens. Protein components of myelin proteins such as myelin basic protein (MBP) (e.g., MBP84-102, MBP83-99, MBP13-32, MBP144-163, MBP143-168, MBP151-170), proteolipid protein (PLP) (e.g., PLP139-151), myelin oligodendrocyte glycoprotein (MOG), myelin-associated glycoprotein (MAG), myelin-associated oligodendrocyte basic protein (MOBP), CNPase (2', 3'-cyclic-nucleotide 3'-phosphodiesterase), S100β protein, and transaldolase H are of particular interest for use according to the invention.

Rheumatoid Arthritis (RA)

Possible candidate autoantigens in RA include collagen type II, human cartilage glycoprotein-39, and aggrecan Gi.

Type 1 Diabetes

Possible candidate autoantigens in Type 1 Diabetes include insulin, proinsulin, glutamic acid decarboxylase 65 (GAD65), insulinoma-associated protein 2 (IA-2), insulinoma-associated protein 2 beta (IA-2beta), islet cell autoantigen (HSP), glima 38, islet cell autoantigen (ICA69), p52, zinc transporter 8 (ZnT8), islet-specific glucose-6-phosphatase catalytic subunit-related protein (IGRP), and chromogranin A.

Myasthenia Gravis

Possible candidate autoantigens in Myasthenia gravis include nAChR, MuSK, and LRP4.

Other autoantigens, in diseases such as MS, RA, Type 1 Diabetes, Myasthenia gravis, IBD, and psoriasis, some of which are listed herein, and others also known in the art, are contemplated for use with the invention. The numbers of known autoantigens and autoimmune epitopes are growing. Any such antigens and epitopes that become known in the future also are contemplated for use with the invention.

The term "disease associated with an autoantigen" or "disease involving an autoantigen" refers to any disease which implicates an autoantigen, e.g. a disease which is characterized by the presence of an immune reaction against an autoantigen or cells expressing an autoantigen.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual, in particular an individual being at risk for the disease. The terms "prophylactic treatment" or "preventive treatment" are used herein interchangeably.

By "being at risk" is meant a subject, i.e. a patient, that is identified as having a higher than normal chance of developing a disease compared to the general population. In addition, a subject who has had, or who currently has, a disease is a subject who has an increased risk for developing a disease, as such a subject may continue to develop a disease.

The term "in vivo" relates to the situation in a subject.

The term "individual" or "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans. Preferably, the term "patient" relates to a diseased individual.

The term "autologous" is used to describe anything that is derived from the same subject. For example, "autologous transplant" refers to a transplant of tissue or organs derived from the same subject Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant A heterologous gene is a gene derived from a source other than the subject.

The agents described herein may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating or preventing a disease or disorder by administration of said pharmaceutical composition to an individual. A pharmaceutical composition is also known in the art as a pharmaceutical formulation. The pharmaceutical composition can be administered locally or systemically.

The term "systemic administration" refers to the administration of a therapeutically effective agent such that the agent becomes widely distributed in the body of an individual in significant amounts and develops a biological effect According to the present invention, it is preferred that administration is by parenteral administration.

The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

The methods of the invention also preferably comprise further providing to the subject an immune inhibiting compound. If the immune inhibiting compound is a peptide or polypeptide it can be provided to the subject by administering the immune inhibiting compound or nucleic acid such as RNA, in particular non-immunogenic RNA such as RNA described herein, encoding the immune inhibiting compound. The immune inhibiting compound can be selected from the group consisting of transforming growth factor beta (TGF-β), interleukin 10 (IL-10), interleukin 1 receptor antagonist (IL-1RA), interleukin 4 (IL-4), interleukin 27 (IL-27), interleukin 35 (IL-35), programmed death-ligand 1 (PD-L1), inducible T-cell co-stimulator ligand (ICOSL), B7-H4, CD39, CD73, FAS, FAS-IL, indoleamine 2,3-dioxygenase 1 (IDO1), indoleamine 2,3-dioxygenase 2 (IDO2), acetaldehyde dehydrogenase 1 (ALDH1)/retinaldehyde dehydrogenase (RALDH), arginase 1 (ARG1), arginase 2 (ARG2), nitrous oxide synthase (NOS2), galectin-1, galectin-9, semaphorin 4A, and any combination thereof. Furthermore, the compositions described herein may comprise such immune inhibiting compound or nucleic acid such as RNA encoding such immune inhibiting compound.

The pharmaceutical composition according to the present invention is generally applied in a "pharmaceutically effective amount" and in "a pharmaceutically acceptable preparation".

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The term "pharmaceutically acceptable" refers to the non-toxicity of a material which does not interact with the action of the active component of the pharmaceutical composition.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one embodiment, the composition is an aqueous composition. The aqueous composition may optionally comprise solutes, e.g. salts. In one embodiment, the composition is in the form of a freeze-dried composition. A freeze-dried composition is obtainable by freeze-drying a respective aqueous composition.

The present invention is further illustrated by the following figures and examples which are not be construed as limiting the scope of the invention.

FIGURES

FIG. 1: Activation of splenic immune cells, cytokine release and expression of protein after administration of luciferase-RNA complexed with F12 liposomes. BALB/c mice (n=7) were injected intravenously into the retro-orbital plexus with 10 μg non-immunogenic LUC mRNA-LPX and investigated 24 hours later (A) for maturation status of dendritic cells (n=3) (revealed by upregulation of CD86), T cells, B cells and NK cells (revealed by upregulation of CD69). 6 hours after mRNA-LPX injection into BALB/c mice (B) serum concentration of IFNα was assessed. (C) Luciferase activity determination in vivo 6, 24, 48 and 72 h after mRNA-LPX-injection into BALB/c mice (n=4) of luciferase-RNA by in vivo bioluminescence imaging. Data are depicted as mean±SD from n=3 mice/group. LLOD=lower limit of detection.

Figure 2:
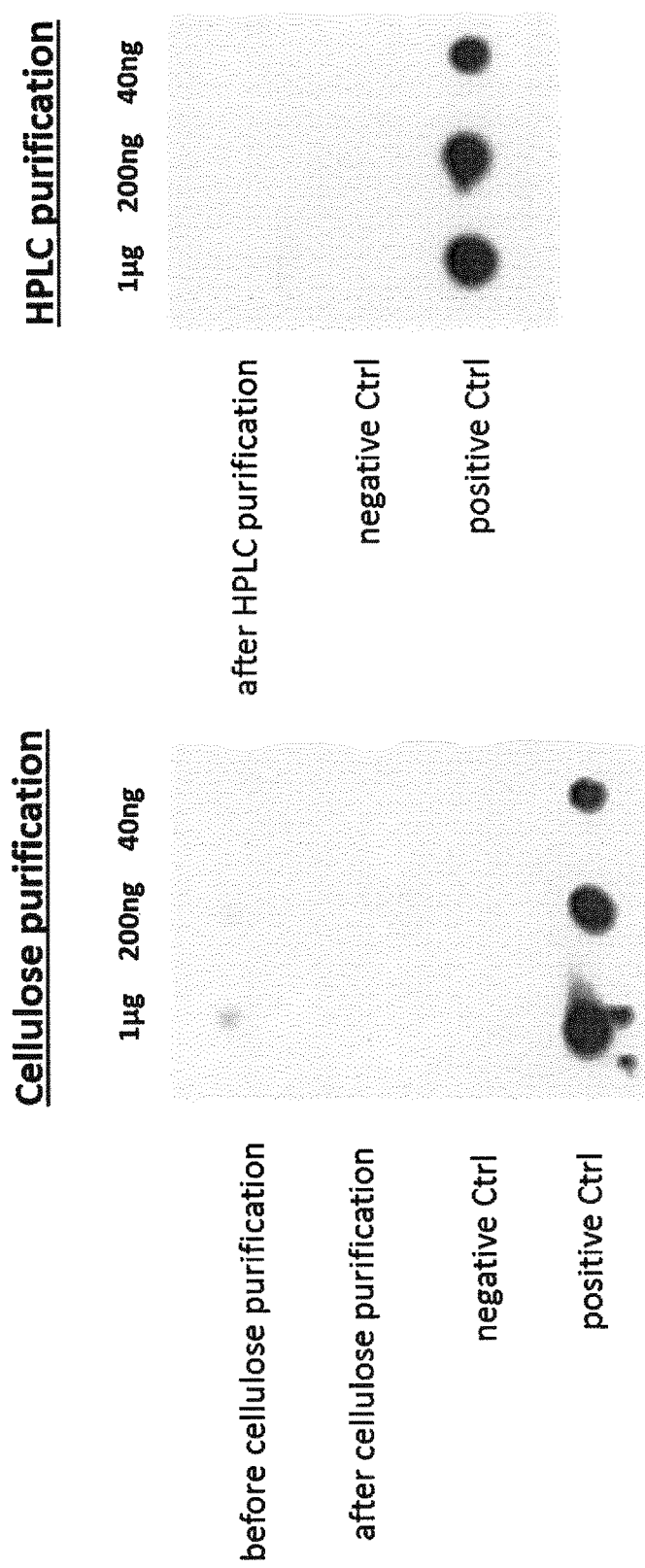

FIG. 2: Dotblot analysis of non-immunogenic MOG35-55 mRNA purified by either Cellulose treatment or HPLC purification. Exposure time 20 sec.

Figure 3:
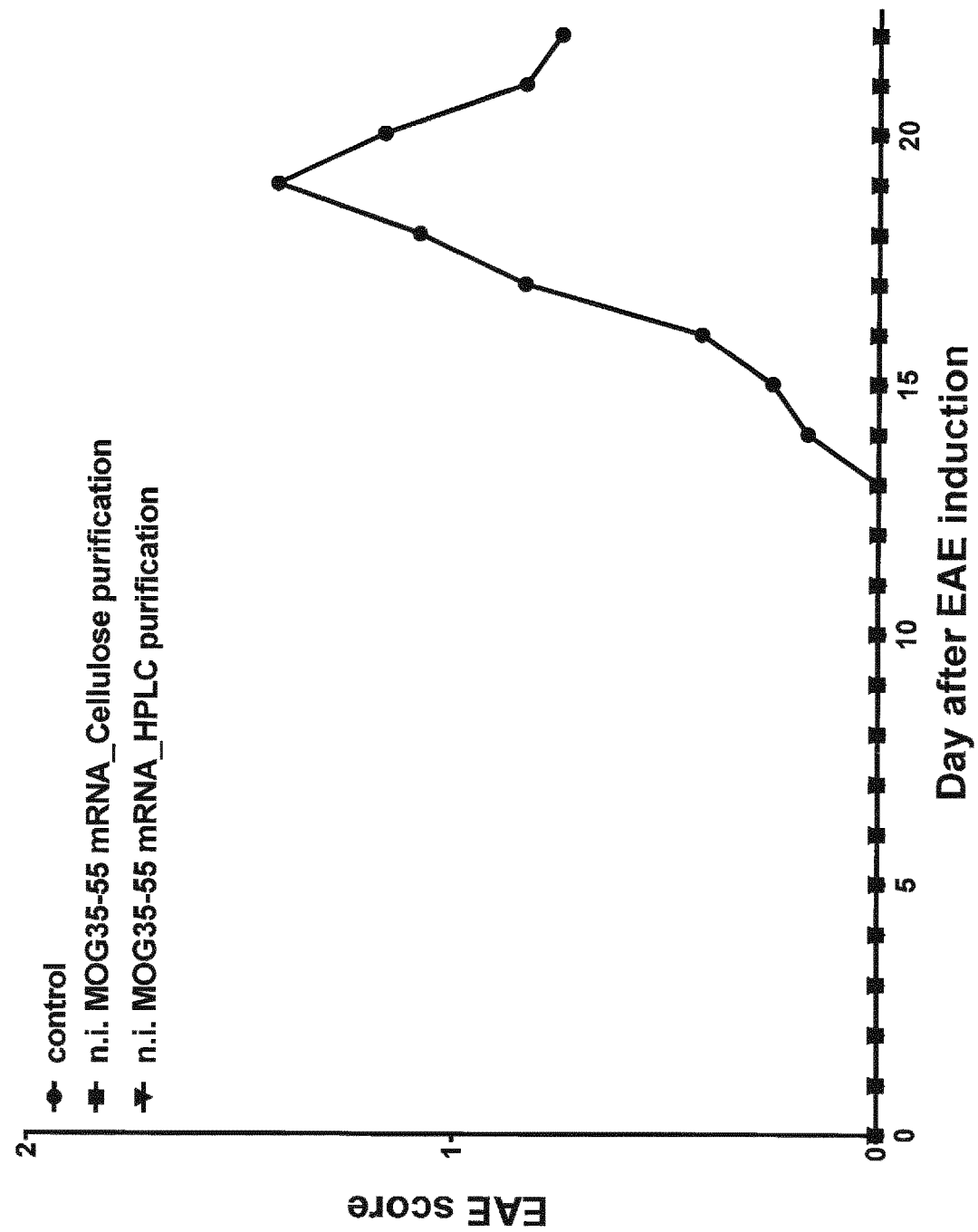

FIG. 3: MOG35-55 antigen presentation by DCs induces tolerance to EAE. EAE was actively induced by immunization with MOG35-55-CFA (day 0) and Pertussis Toxin (days 0 and 2) in C57BL/6 mice. Non-immunogenic MOG35-55 coding mRNA, purified either by Cellulose or HPLC method, was injected intravenously into the retro-orbital plexus at day 7 and day 10 after EAE induction. Control mice received 150 mM NaCl. Data are depicted as mean. n=6 mice/group.

Figure 4:
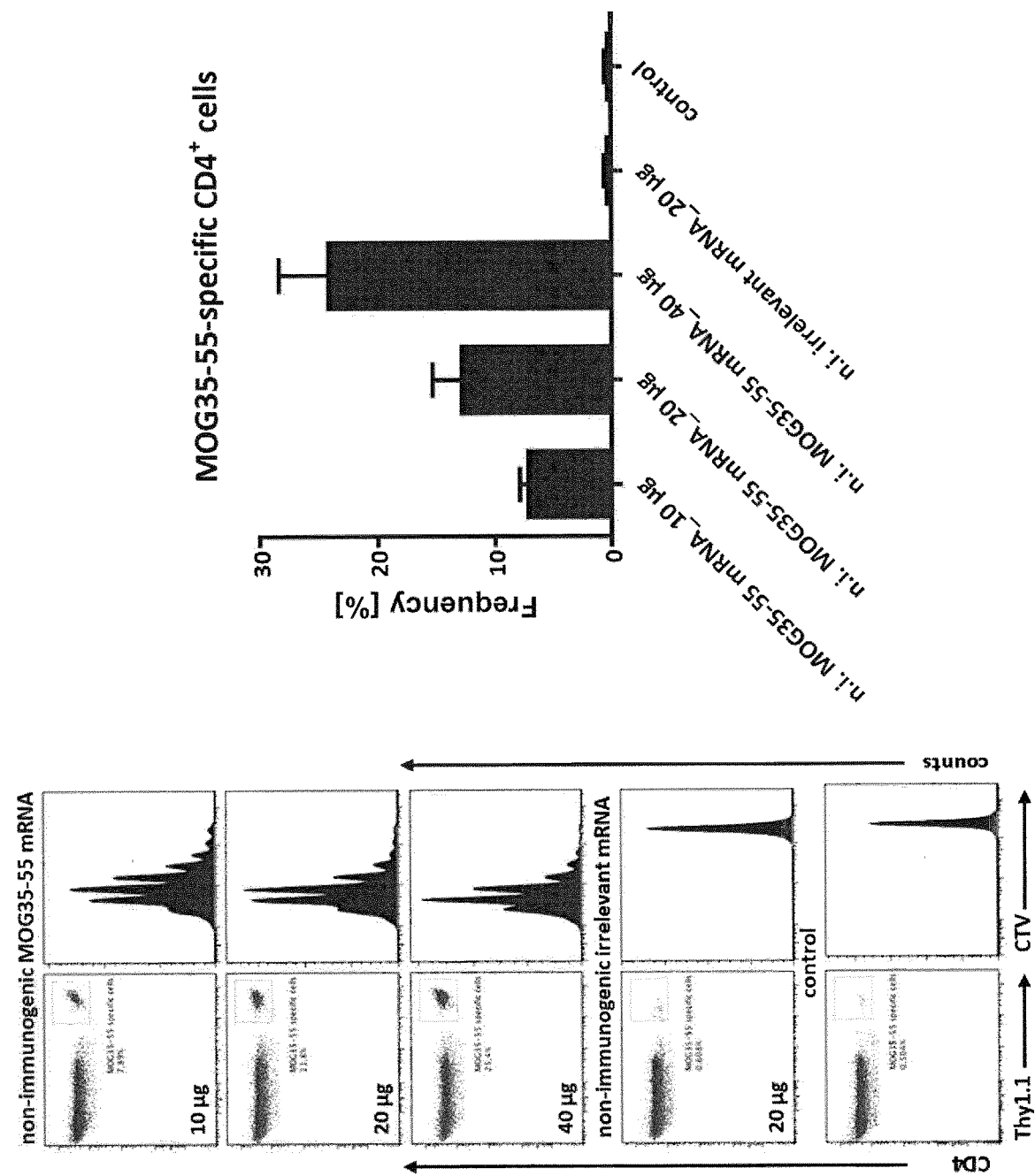

FIG. 4: MOG35-55 antigen presentation by APCs induces antigen-specific T cell proliferation. Naïve, cell-trace-violet (CTV) labeled, Thy1.1$^+$ 2D2$^+$ CD4$^+$ T cells were adoptively transferred to Thy1.2$^+$ C57BL/6 control mice. At the next day, mice were immunized with 10, 20 or 40 μg of non-immunogenic MOG35-55 coding mRNA. Control mice were treated with 20 μg non-immunogenic irrelevant control mRNA. A second control group received furthermore 150 mM NaCl. 4 days later, mice were sacrificed and spleen was analyzed for proliferating Thy1.1$^+$ cells. Data are depicted as mean±SD from n=3 mice/group.

Figure 5:
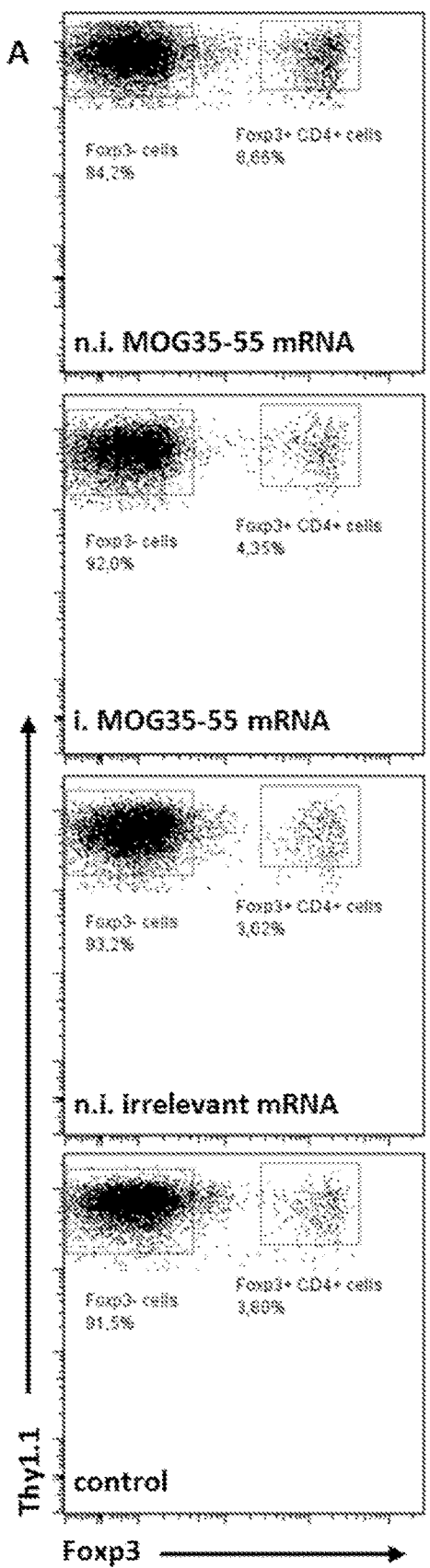
Figure 5:
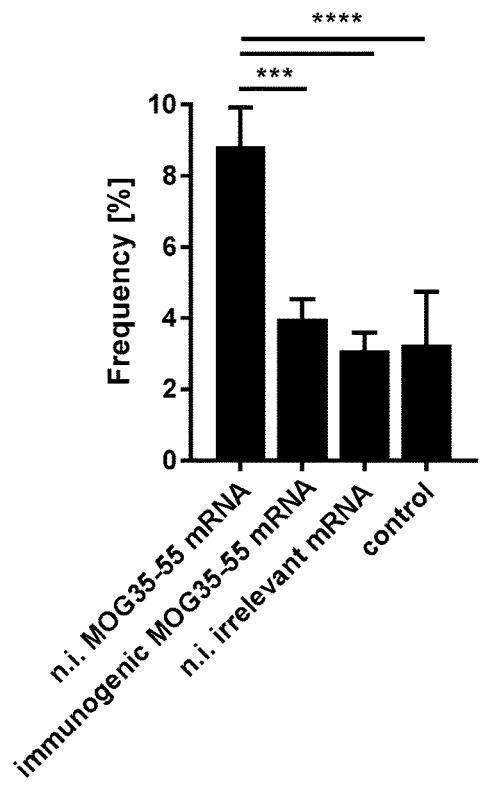
Figure 5:
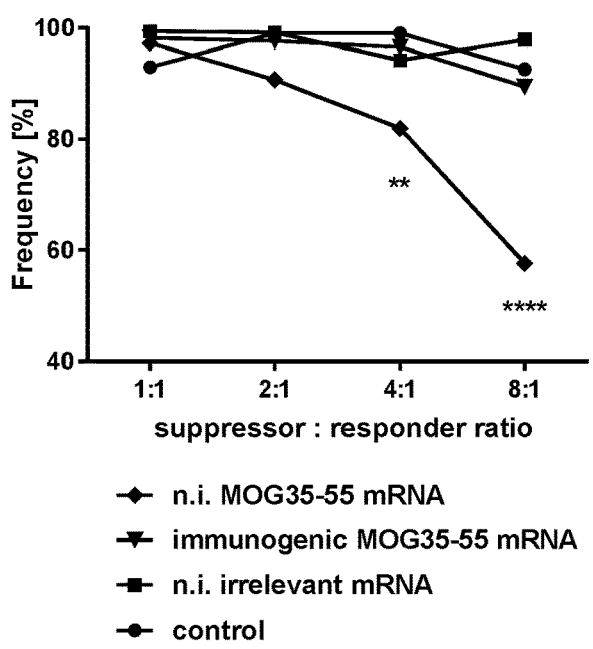

FIG. 5: In vitro suppression of MOG35-55 T cell proliferation by induced antigen-specific Treg cells. (A, B) 2D2 Foxp3-eGFP mice were immunized 4 times (d0, d3, d6, d9) with non-immunogenic MOG35-55 coding mRNA. Control mice were treated with immunogenic MOG35-55 coding mRNA or non-immunogenic irrelevant control mRNA. A third control group received furthermore 150 mM NaCl. 4 days after the last mRNA treatment mice were sacrificed and MOG35-55 specific CD4$^+$ cells were analyzed for Foxp3-eGFP expression (C). Cells of each treatment group (suppressors) were co-cultured with CTV labeled 2D2 CD4$^+$ T cells of untreated naïve mice (responder cells) and restimulated in vitro with MOG35-55 peptide-loaded BMDCs for 72 h. Proliferation of responder cells was determined by CTV dilution by FACS (gated on CTV$^+$ cells). The inhibitory capacity of suppressor cells was measured at 4 different ratios to responder cells. Data are depicted as mean±SD from n=4 mice/group. Statistical analysis of frequency of CD4$^+$ Foxp3$^+$ cells was assessed via one-way ANOVA and Tukey's multiple comparison test, ***p≤0.001.

Figure 6:
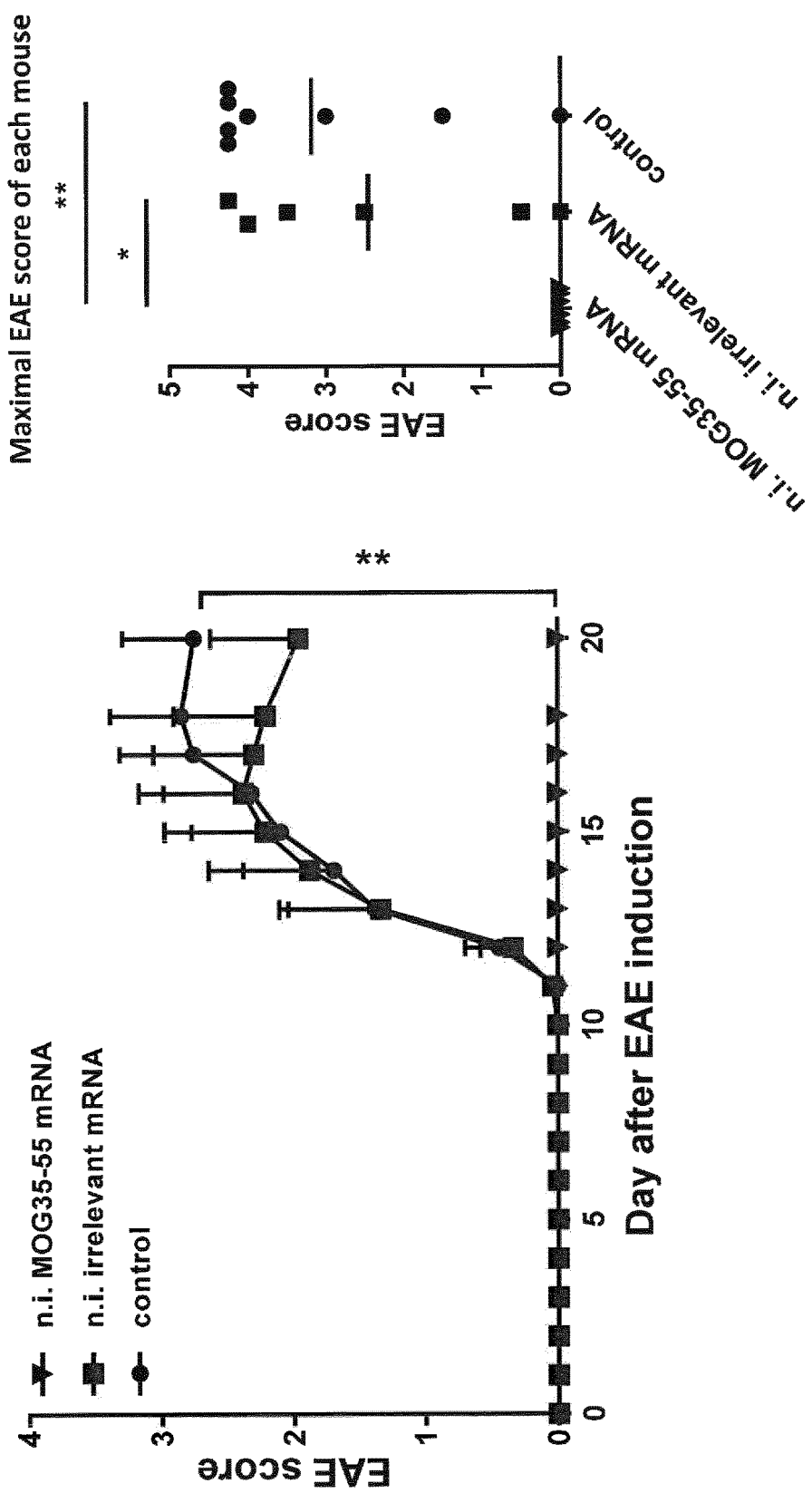

FIG. 6: MOG35-55 antigen presentation by DCs induces tolerance to EAE. EAE was actively induced by immunization with MOG35-55-CFA (day 0) and Pertussis Toxin (days 0 and 2) in C57BL/6 mice. Non-immunogenic MOG35-55 coding mRNA, as well as non-immunogenic irrelevant mRNA were injected intravenously into the retro-orbital plexus at day 7 and day 10 after EAE induction. Control mice received 150 mM NaCl. Data are depicted as mean. n=6-8 mice/group. Statistical analysis of maximal EAE score of each mouse per group was determined via one-way ANOVA and Tukey's multiple comparison test. Area under curve (AUC) was used to determine statistical significance via one-way ANOVA and Tukey's multiple comparison test of the different EAE disease development curves.

Figure 7:
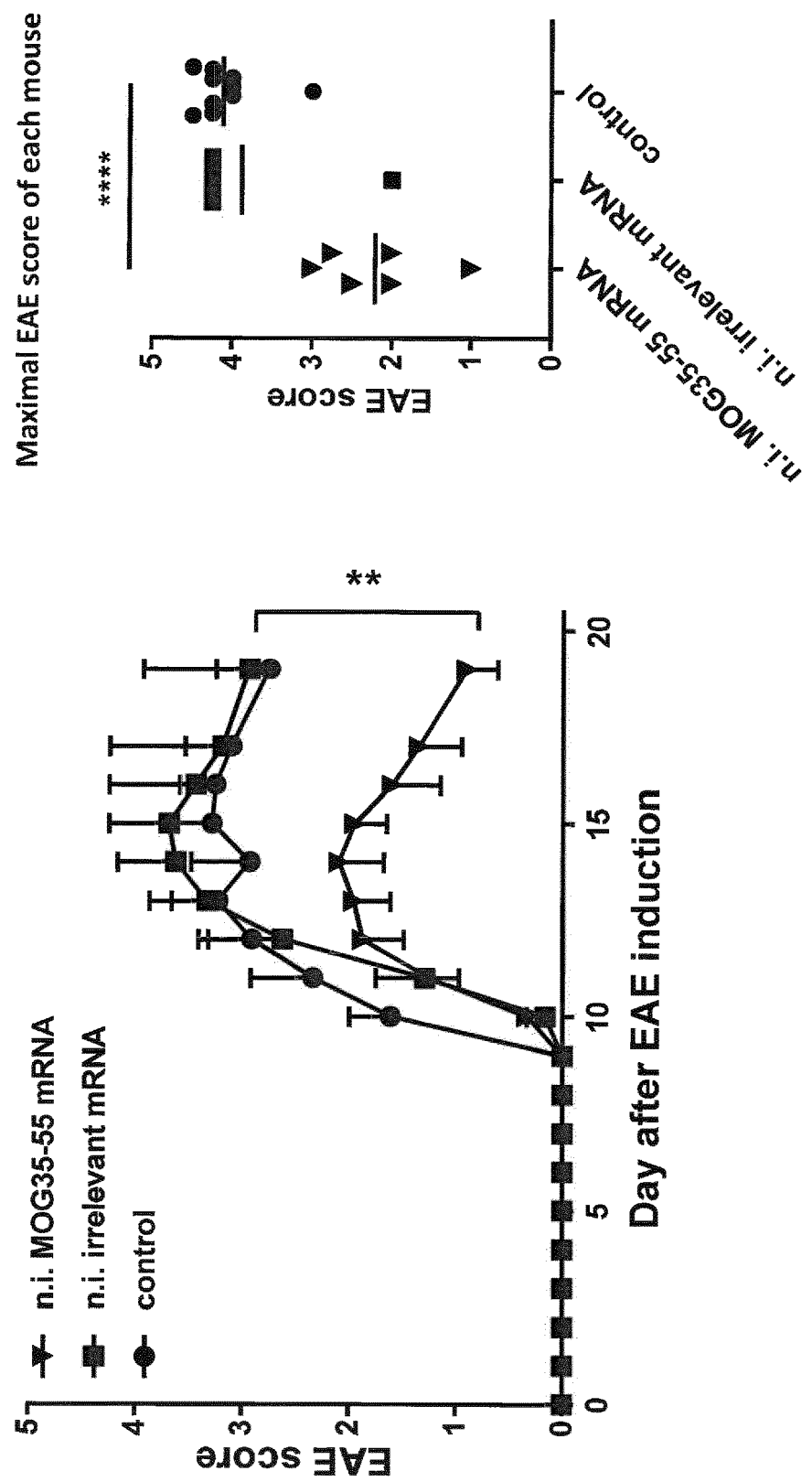

FIG. 7: MOG35-55 antigen presentation by DCs induces tolerance to EAE in a real therapeutic setting. EAE was actively induced by immunization with MOG35-55-CFA (day 0) and Pertussis Toxin (days 0 and 2) in C57BL/6 mice. Non-immunogenic MOG35-55 coding mRNA, as well as non-immunogenic irrelevant mRNA were injected intravenously into the retro-orbital plexus after mice reached an EAE score of 1-2. Control mice received 150 mM NaCl. Data are depicted as mean. n=6-9 mice/group. Statistical analysis of maximal EAE score of each mouse per group was assessed via one-way ANOVA and Tukey's multiple comparison test Area under curve (AUC) was used to determine statistical significance via one-way ANOVA and Tukey's multiple comparison test of the different EAE disease development curves.

Figure 8:
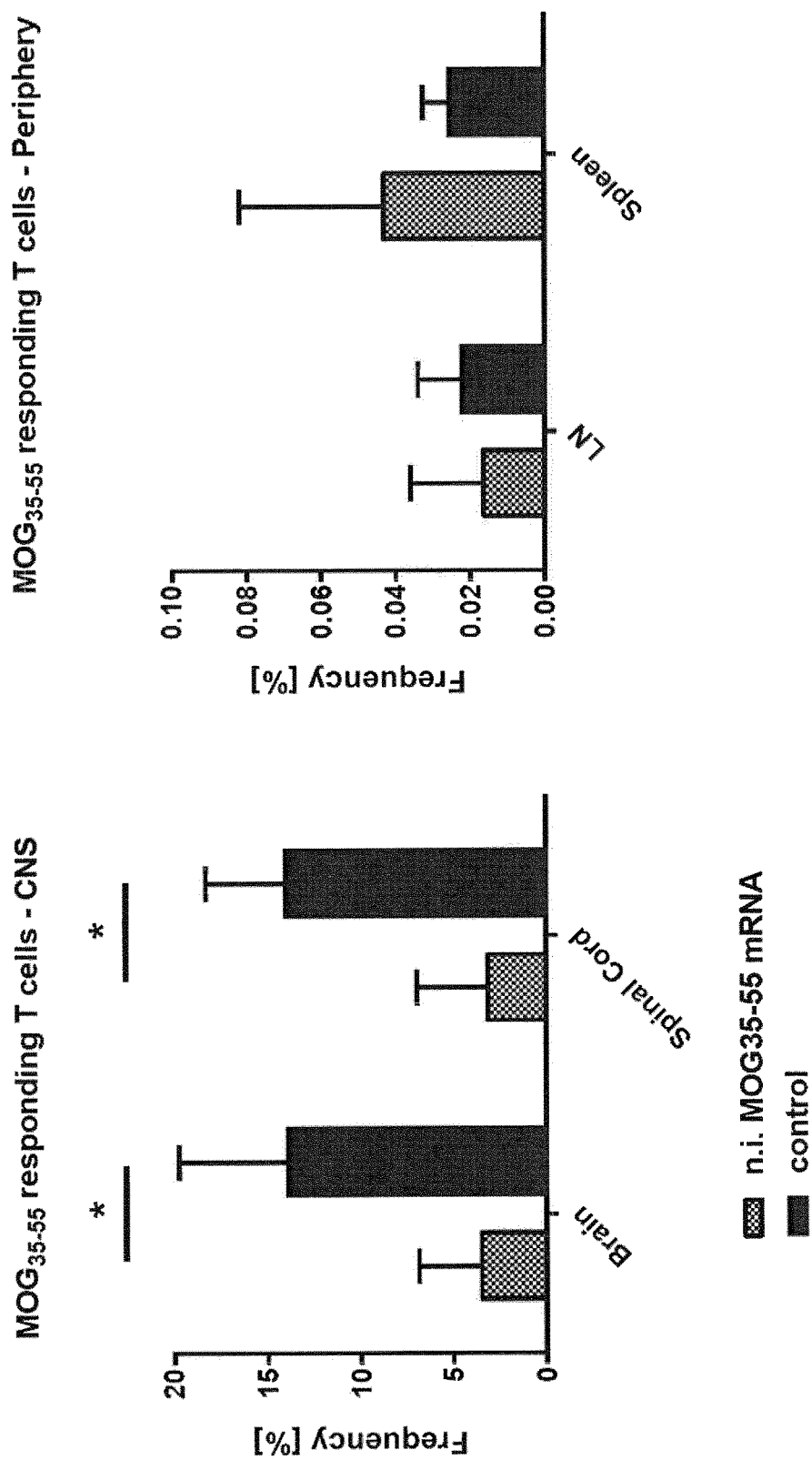

FIG. 8: Antigen presentation by DCs induces tolerance to EAE. EAE was actively induced by immunization with MOG35-55-CFA in C57BL/6 mice and mice were treated at day 7 and day 10 after EAE induction with 20 μg of non-immunogenic MOG35-55-coding mRNA or 150 mM NaCl. At day 16 after disease induction organs were taken from EAE afflicted and mRNA treated mice and were cultured in the presence of MOG35-55 peptide for 6 h in the presence of Brefeldin A. The expression of CD40L was examined by intracellular cytokine staining of CD4+CD44$^+$ T cells. Data are depicted as mean±SD from n=4 mice/group. Statistical analysis of CD4$^+$ Teff cells was assessed via one-way ANOVA and Tukey's multiple comparison test, *p≤0.05.

Figure 9:
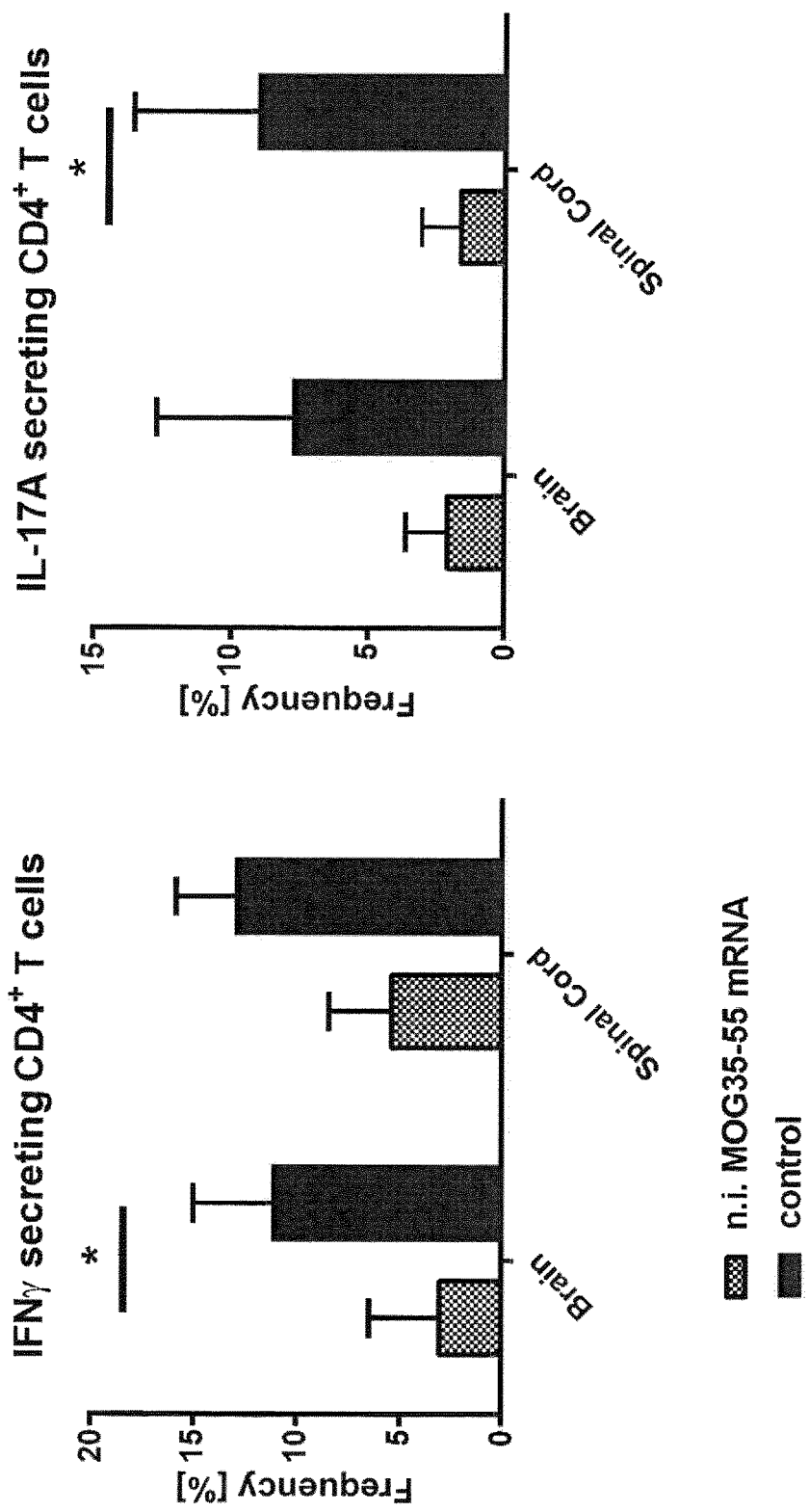

FIG. 9: MOG35-55 peptide specific Th1 and Th17 cells are significantly reduced in therapeutically treated mice (day 7/day 10). EAE was actively induced by immunization with MOG35-55-CFA in C57BL/6 mice and mice were treated at day 7 and day 10 after EAE induction with 20 μg of non-immunogenic MOG35-55-coding mRNA or 150 mM NaCl. Brain and spinal cord were harvested at day 16 after EAE induction and cells restimulated in vitro in the presence of MOG35-55 peptide for 6 h in the presence of Brefeldin A. CD4$^+$ T cells were then analyzed for their expression of IFNγ and IL-17A by intracellular cytokine staining and percentages of IFNγ$^+$ and IL-17A$^+$ CD4$^+$ T cells were calculated. Data are depicted as mean SD from n=4 mice/group. Statistical analysis was evaluated by one-way ANOVA and Tukey's multiple comparison test, *p≤0.05.

Figure 10:
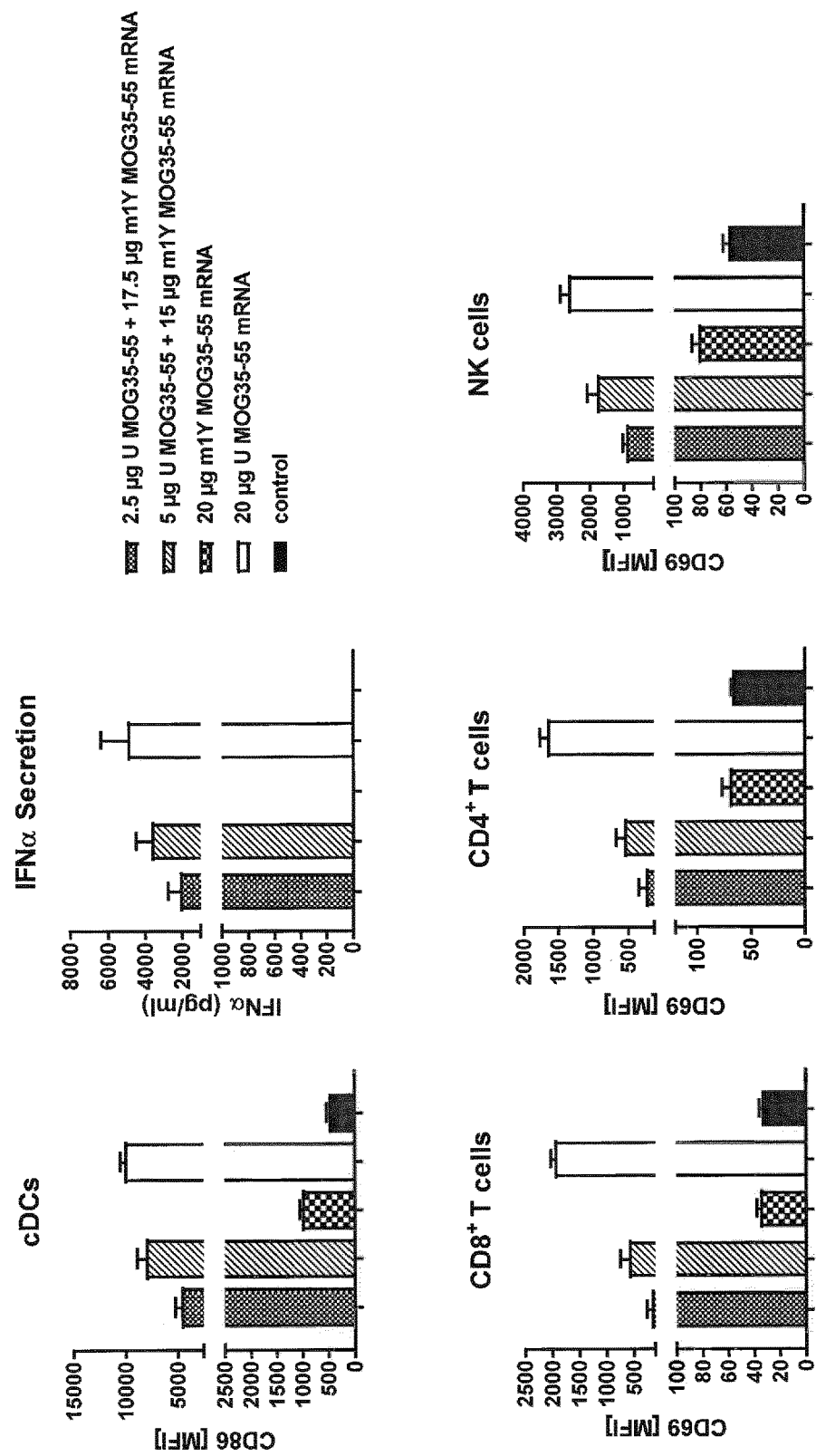

FIG. 10: Activation of splenic immune cells and cytokine release after administration of different MOG35-55-mRNA mixes of non-immunogenic (m1Y) and immunogenic (U) mRNA complexed with F12 liposomes. C57BL/6 mice were injected intravenously into the retro-orbital plexus with 20

μg total MOG35-55 mRNA-LPX and investigated 24 hours later for maturation status of dendritic cells (revealed by upregulation of CD86), T cells and NK cells (revealed by upregulation of CD69). 6 hours after mRNA-LPX injection into C57BL/6 mice serum concentration of IFNα was assessed. Data are depicted as mean±SD from n=3 mice/group.

Figure 11:
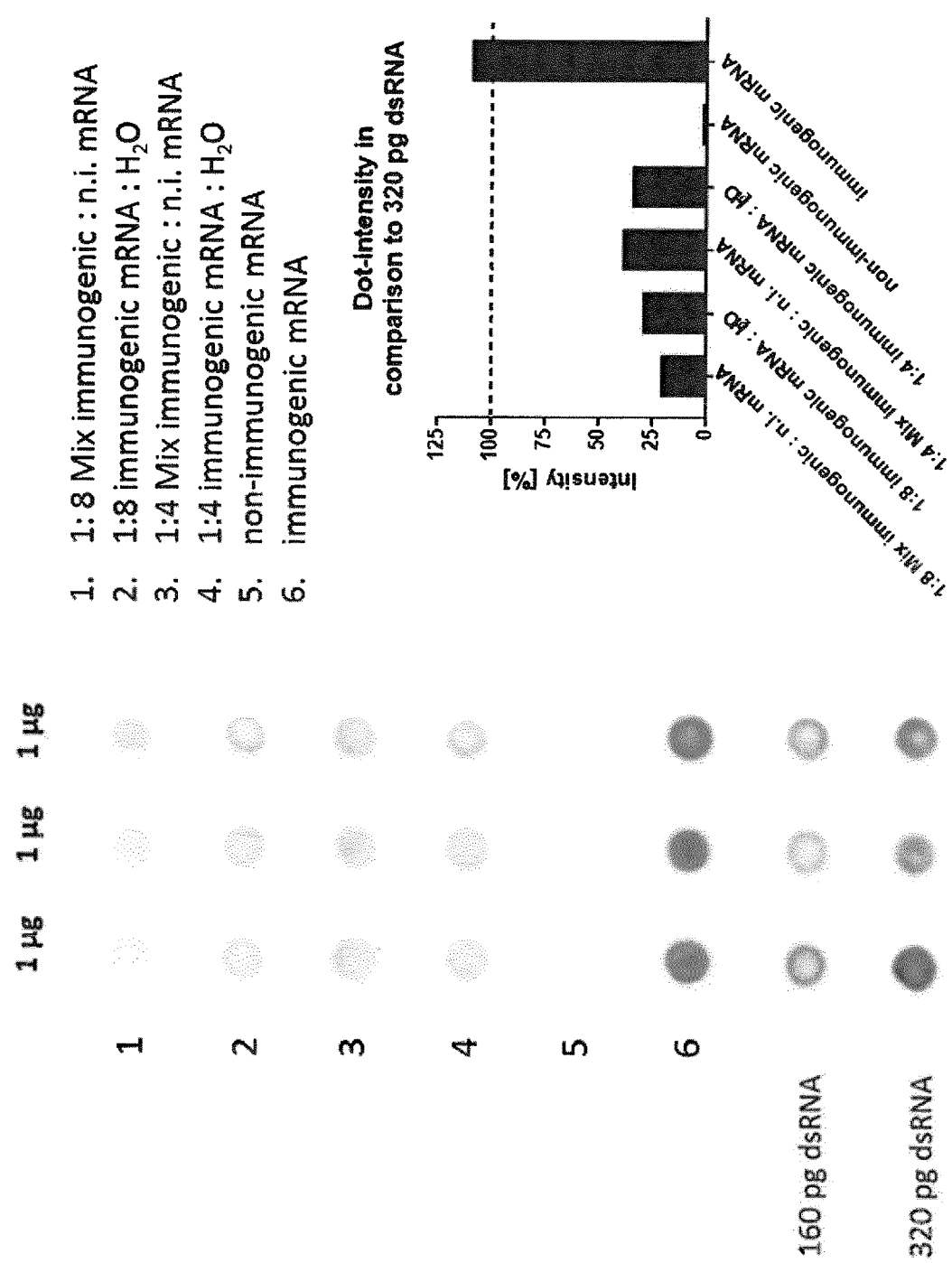

FIG. 11: Dotblot analysis of different MOG35-55-mRNA mixtures of non-immunogenic and immunogenic mRNA. Exposure time 20 sec. Dashed line is set as 100% of Dot-intensity for 320 μg of dsRNA.

Figure 12:
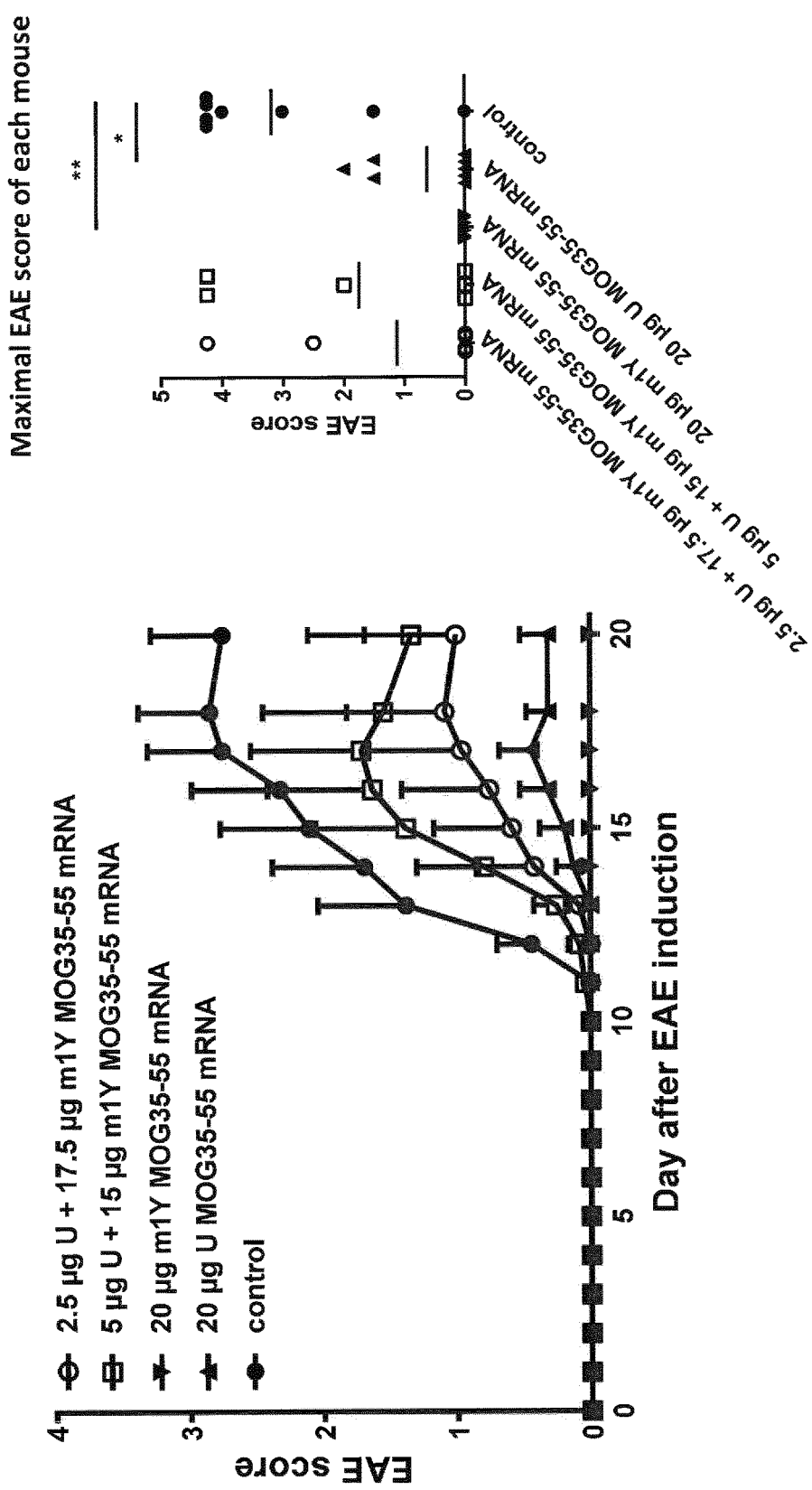

FIG. 12: Non-immunogenic MOG35-55 mRNA induces full tolerance to EAE. EAE was actively induced by immunization with MOG35-55-CFA (day 0) and Pertussis Toxin (days 0 and 2) in C57BL/6 mice. Different mixtures of non-immunogenic (m1Y) and immunogenic (U) MOG35-55 coding mRNAs were injected intravenously into the retro-orbital plexus at day 7 and day 10 after EAE induction. Control mice received 150 mM NaCl. Data are depicted as mean. n=6-8 mice/group. Statistical analysis of maximal EAE score of each mouse per group was assessed via one-way ANOVA and Tukey's multiple comparison test, **$p \leq 0.01$.

Figure 13:
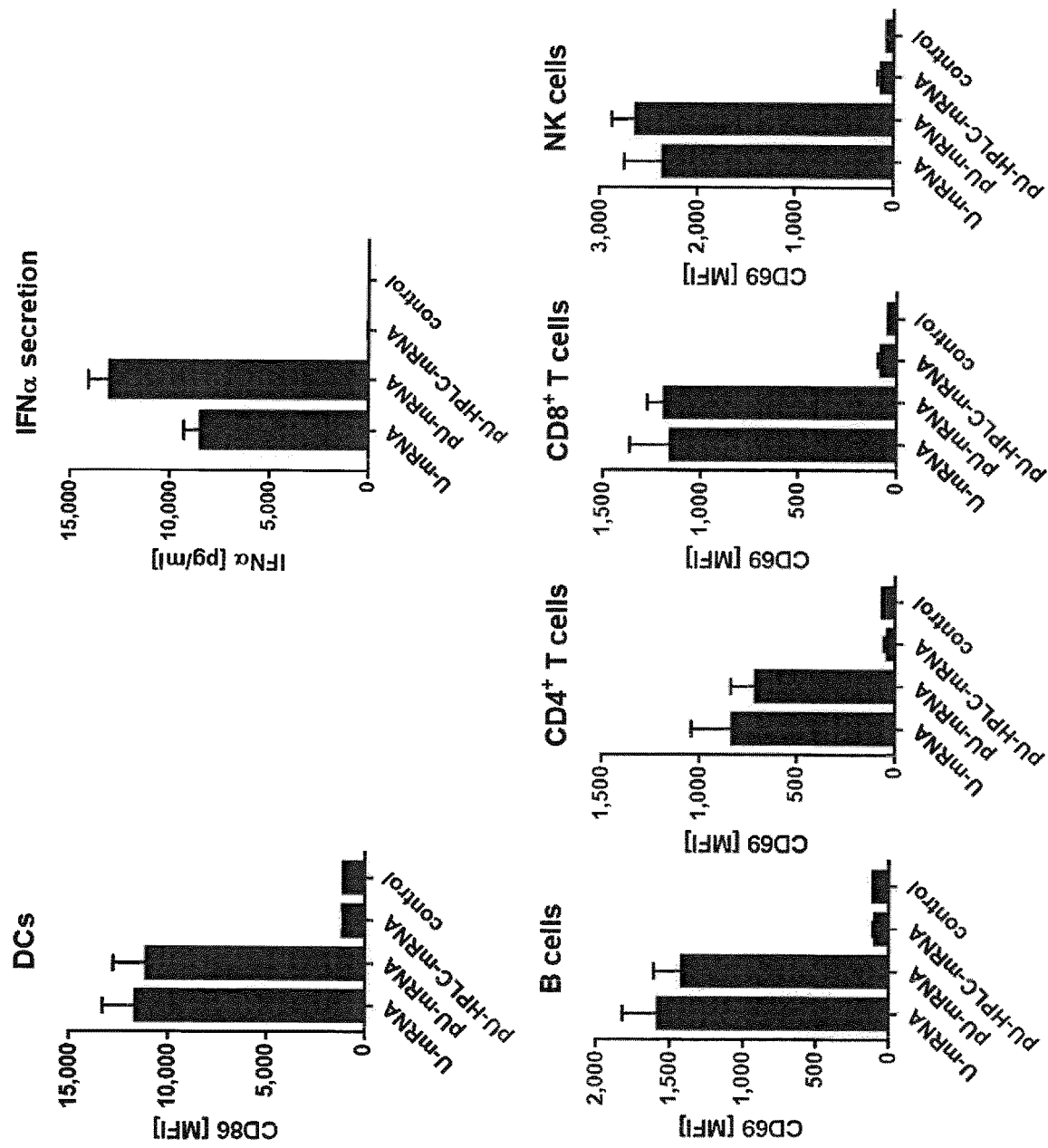

FIG. 13: Nucleoside-modification alone does not induce a loss of recognition. Activation of splenic immune cells and cytokine release after administration of different nucleoside-modified mRNAs complexed with F12 liposomes. C57BL/6 mice were injected intravenously into the retro-orbital plexus with 10 μg total mRNA-LPX and investigated 24 hours later for maturation status of dendritic cells (revealed by upregulation of CD86), T cells and NK cells (revealed by upregulation of CD69). 6 hours after mRNA-LPX injection into C57BL/6 mice serum concentration of IFNα was assessed. Data are depicted as mean±SD from n=3 mice/group.

Figure 14:
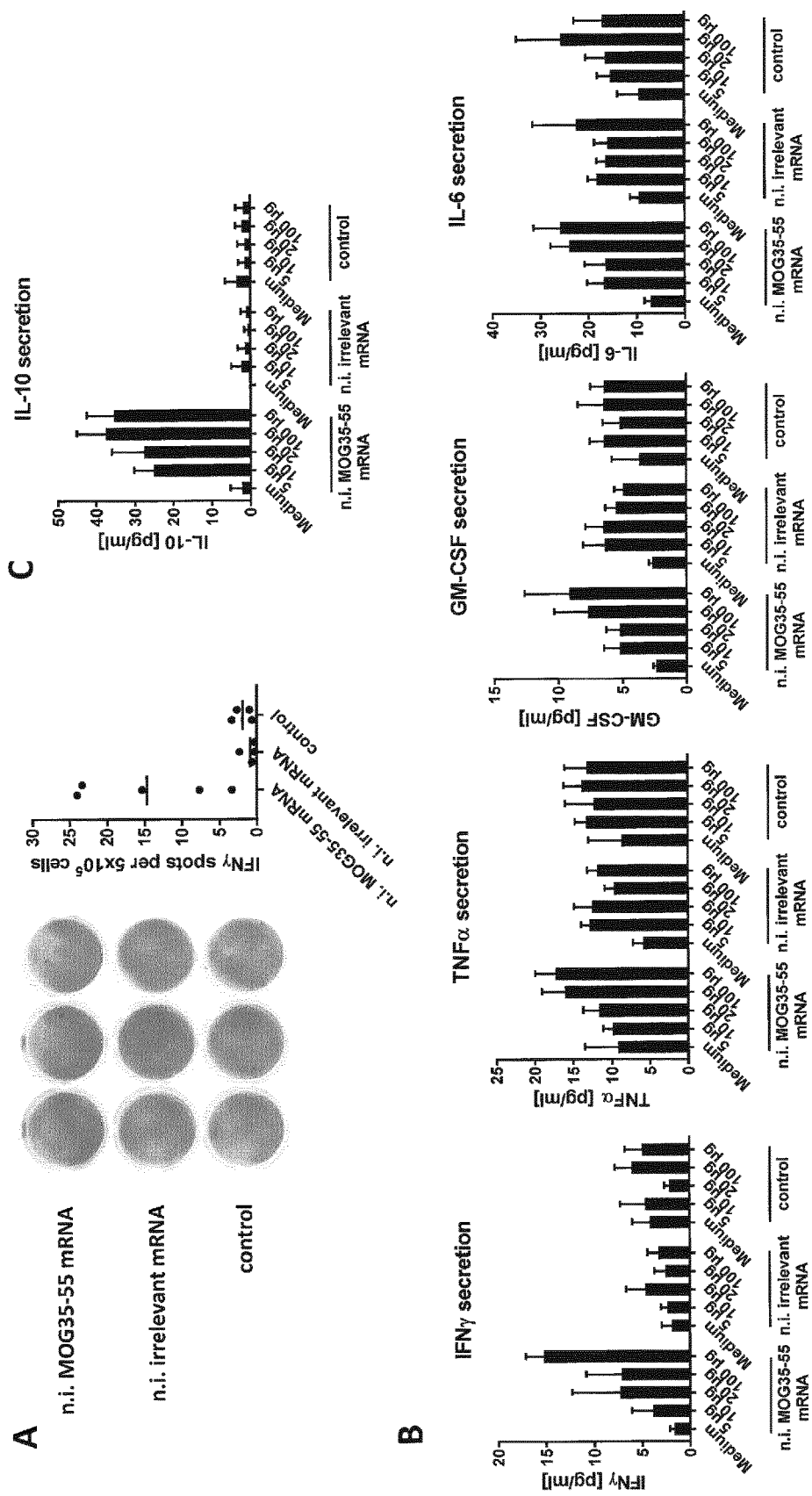

FIG. 14: Non-immunogenic MOG35-55 coding mRNA-LPX treatment does not lead to expansion of antigen-specific CD4$^+$ effector cells. Naïve C57BL/6 mice were treated at day 0, 3, 7 and 10 with 20 μg non-immunogenic MOG35-55 coding mRNA. Control mice were treated with 20 μg non-immunogenic irrelevant control mRNA. A second control group received 150 mM NaCl. At day 13 after the first mRNA treatment, mice were sacrificed and splenocytes were analyzed for secretion of pro- and anti-inflammatory cytokines by IFNγ ELISpot (A) and detection of cytokines by Multiplex ELISA in the supernatant of MOG35-55-peptide restimulated cells (B and C). Data are depicted as mean±SD from n=4-5 mice/group.

Figure 15:
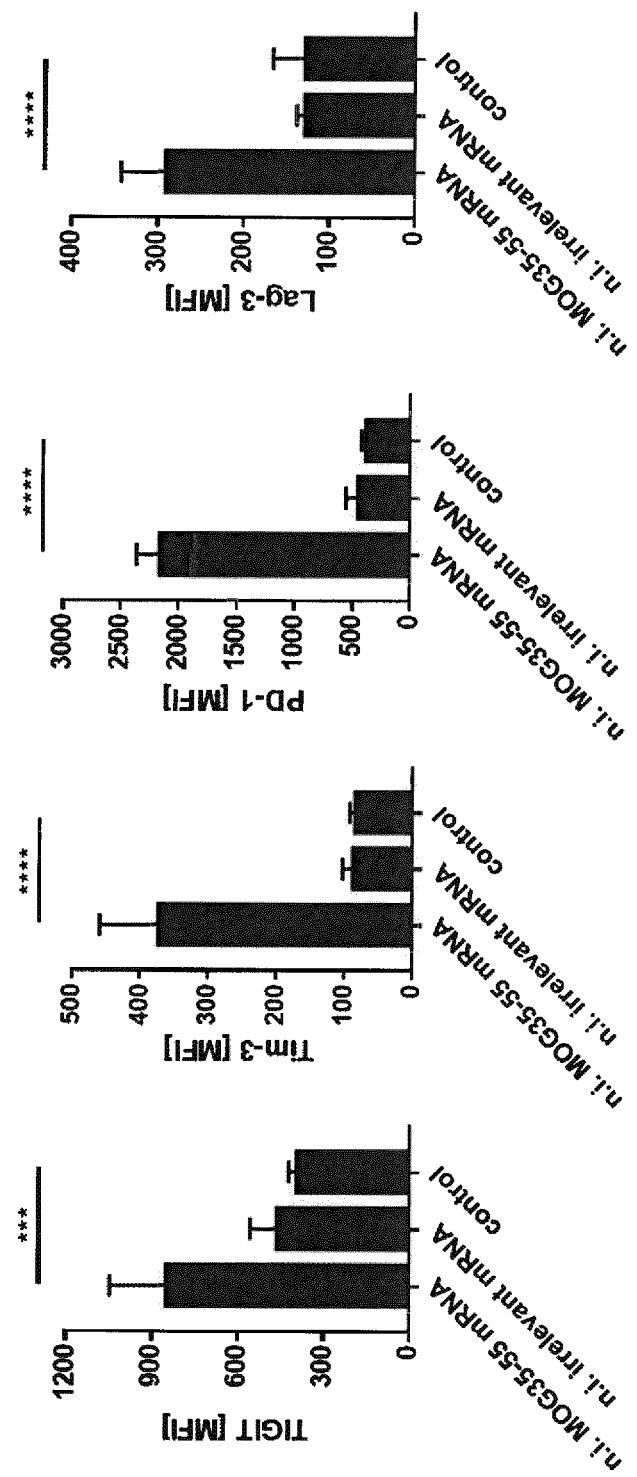

FIG. 15: Co-inhibitory molecules are upregulated upon treatment with non-immunogenic MOG35-55 coding mRNA-LPX. Naïve C57BL/6 mice were treated at day 0, 3, 7 and 10 with 20 μg non-immunogenic MOG35-55 coding mRNA. Control mice were treated with 20 μg non-immunogenic irrelevant control mRNA. Furthermore, a second control group received 150 mM NaCl. At day 13 after the first mRNA treatment, mice were sacrificed and MOG35-55 CD4$^+$ T cells from the spleen were analyzed by flow cytometry for upregulation of co-inhibitory molecules. Data are depicted as mean±SD from n=4-5 mice/group. Statistical analysis was assessed via one-way ANOVA and Tukey's multiple comparison test.

Figure 16:
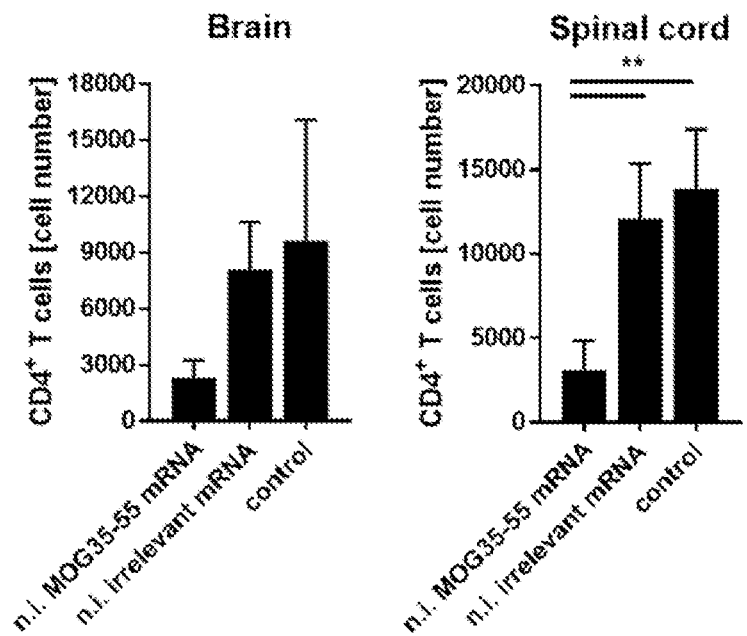
Figure 16:
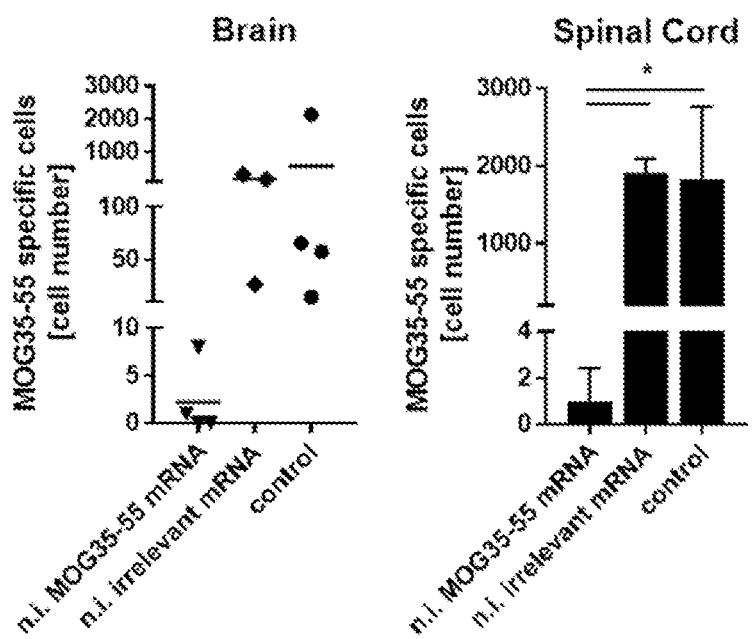

FIG. 16: Therapeutic vaccination with non-immunogenic MOG35-55 coding mRNA-LPX reduces infiltration of lymphocytes into the CNS. Naïve Thy1.1$^+$ 2D2 CD4$^+$ T cells were adoptively transferred into Thy1.2$^+$ C57BL/6 mice at d-1. EAE was actively induced the day after by immunization with MOG35-55-CFA (day 0) and Pertussis Toxin (day 0 and 2) and mice were treated at day 7 and day 10 after EAE induction with 20 μg non-immunogenic MOG35-55-coding mRNA, 20 μg non-immunogenic irrelevant mRNA or 150 mM NaCl. At day 16 after disease induction organs were taken from differently treated mice. The infiltration of Thy1.1$^+$ CD4$^+$ MOG35-55 specific cells was examined and the total number of infiltrating cells was determined via flow cytometry using Trucount™ tubes. Data are depicted as mean±SD from n=4 mice/group. Statistical analysis of infiltrated CD4$^+$ Teff cells was assessed via one-way ANOVA and Tukey's multiple comparison test.

Figure 17:
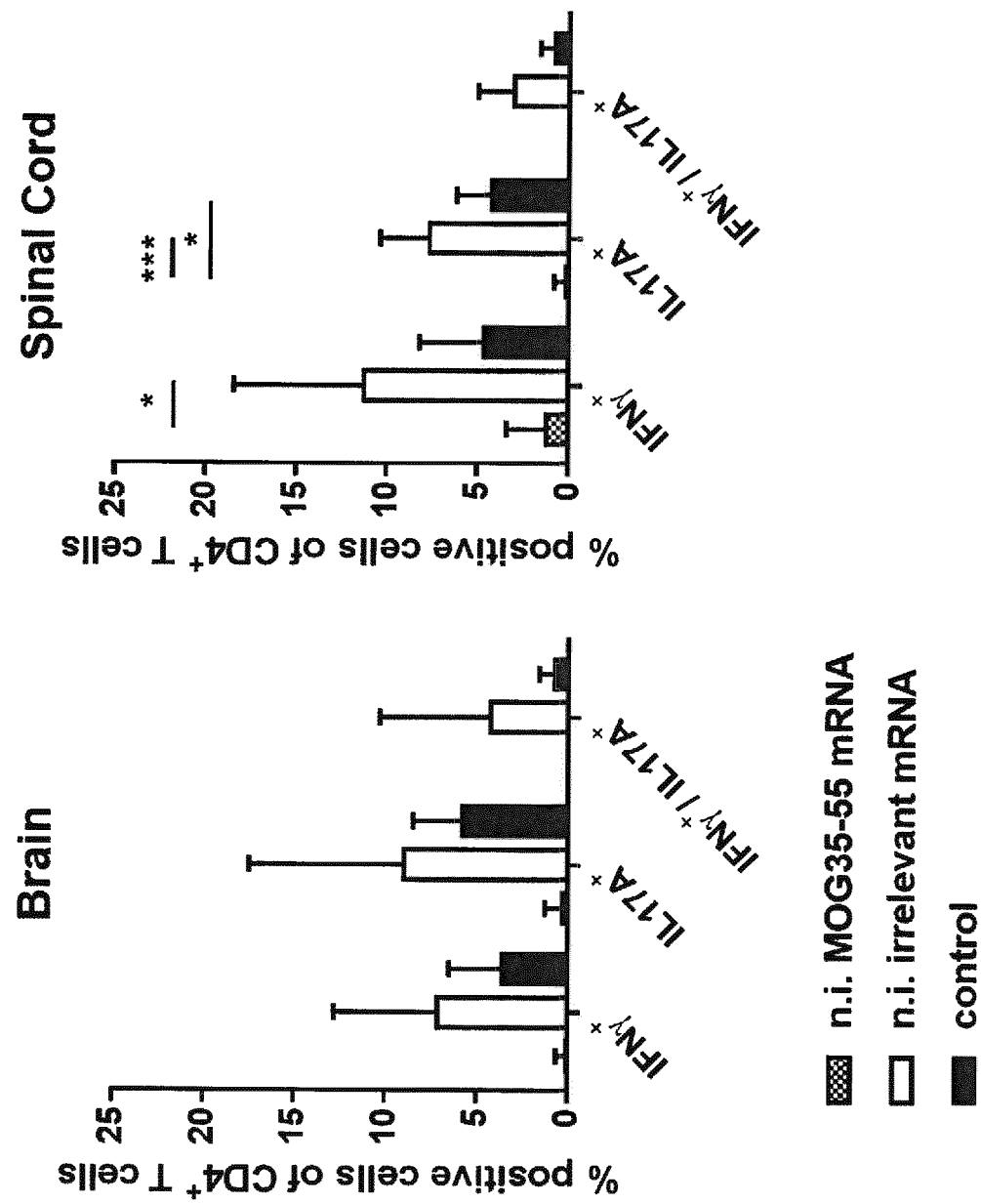

FIG. 17: MOG35-55 specific Th1 and Th17 cells are significantly reduced in therapeutically treated mice (day 7/day 10). EAE was actively induced by immunization with MOG35-55-CFA (day 0) and Pertussis Toxin (day 0 and 2) in C57BL/6 mice and mice were treated at day 7 and day 10 after EAE induction with 20 μg non-immunogenic MOG35-55-coding mRNA, 20 μg non-immunogenic irrelevant mRNA or 150 mM NaCl. Brain and spinal cord were harvested at day 16 after EAE induction and cells were restimulated in vitro in the presence of MOG35-55 peptide for 6 h in the presence of Brefeldin A. CD4$^+$ T cells were then analyzed by flow cytometry for their expression of IFNγ and IL-17A by intracellular cytokine staining and percentages of IFNγ$^+$ and IL-17A$^+$ of CD4$^+$ T cells were calculated. Data are depicted as mean±SD from n=4 mice/group. Statistical analysis was evaluated by one-way ANOVA and Tukey's multiple comparison test.

Figure 18:
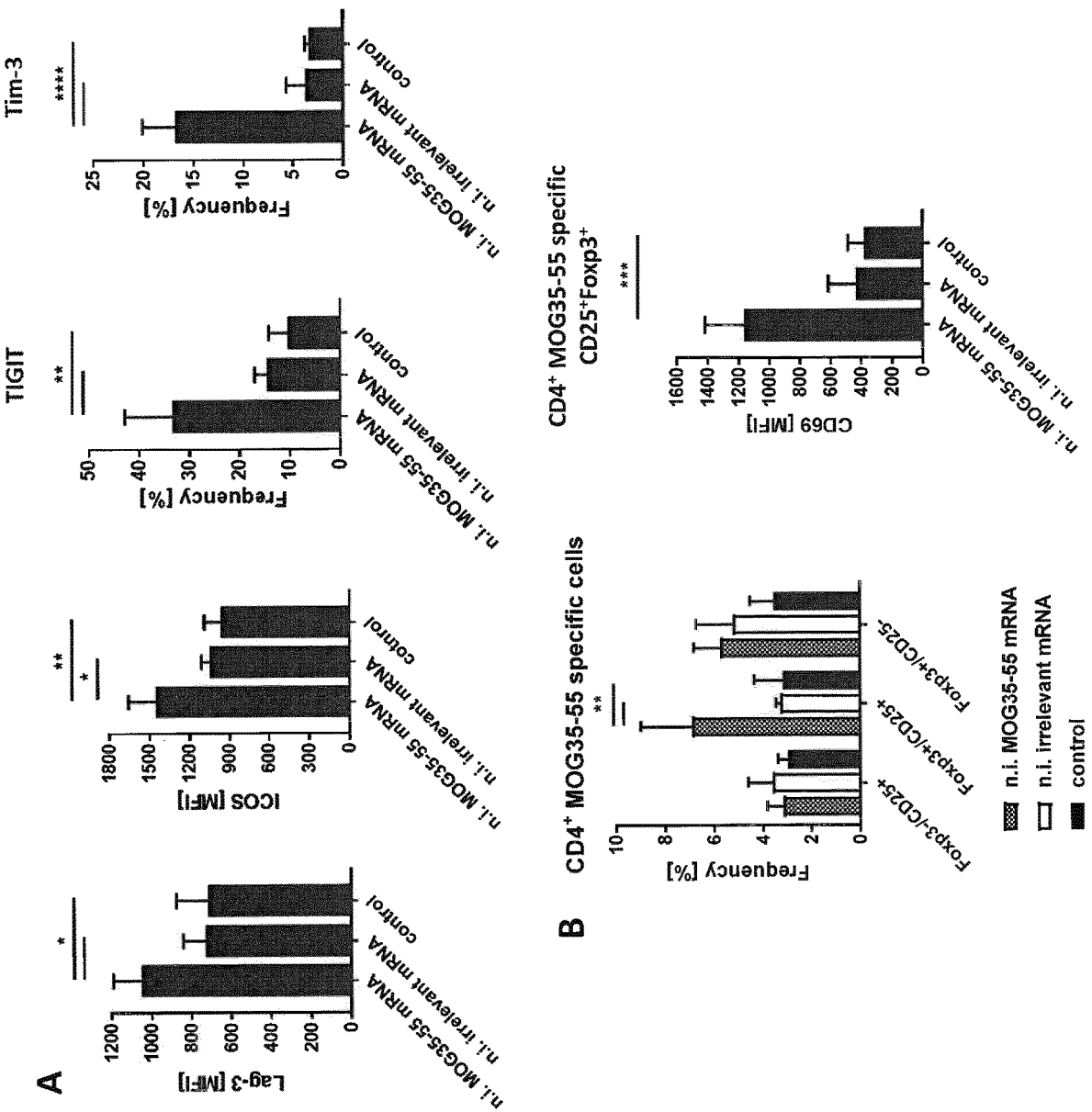

FIG. 18: Co-inhibitory molecules are upregulated on MOG35-55-specific CD4$^+$ T cells upon successful non-immunogenic MOG35-55-specific mRNA-LPX treatment EAE was actively induced by immunization with MOG35-55-CFA (day 0) and Pertussis Toxin (day 0 and 2) in C57BL/6 mice and mice were treated at day 7 and day 10 after EAE induction with 20 μg non-immunogenic MOG35-55-coding mRNA, 20 μg non-immunogenic irrelevant mRNA or 150 mM NaCl. At day 16 after disease induction spleens were dissected from differently treated groups. MOG35-55 specific CD4$^+$ T cells were isolated by tetramer-specific MACS and phenotypically analyzed via flow cytometry by tetramer staining. Data are depicted as mean±SD from n=4 mice/group. Statistical analysis was evaluated by one-way ANOVA and Tukey's multiple comparison test.

Figure 19:
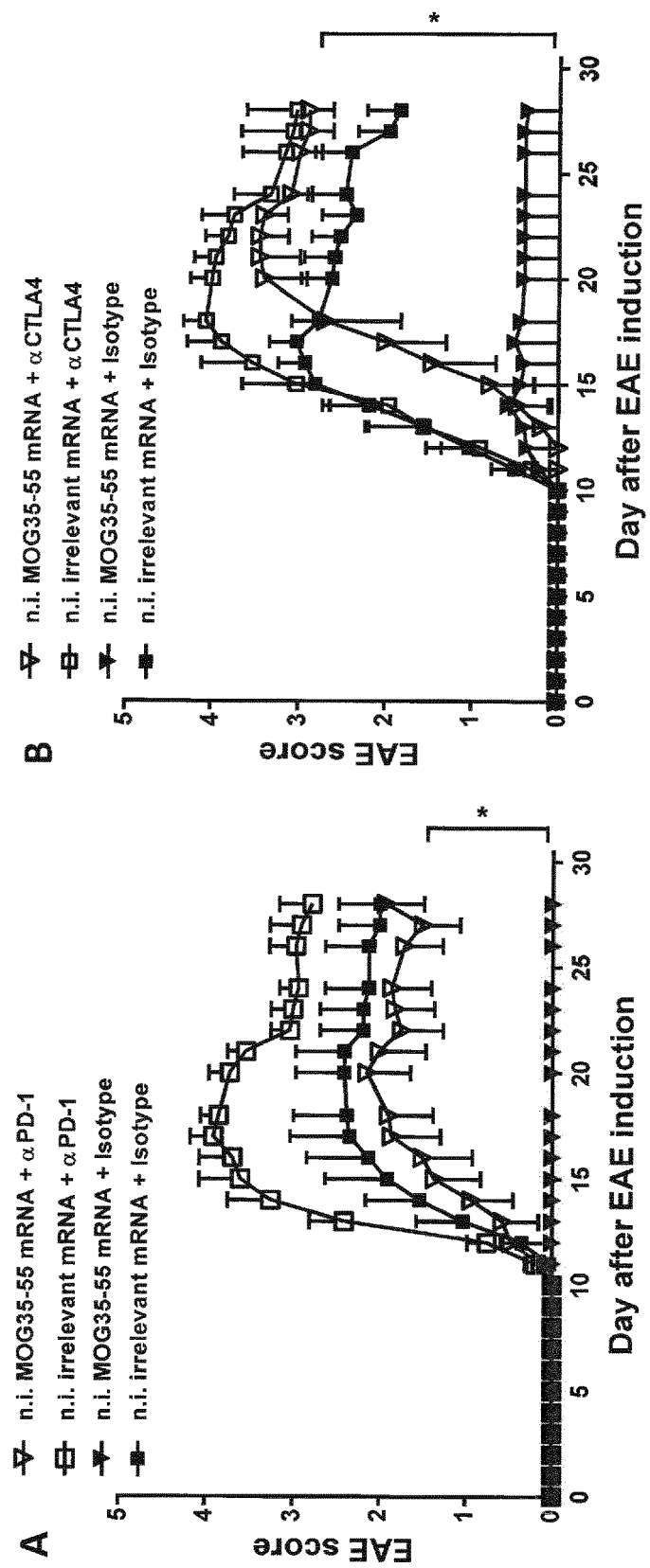

FIG. 19: PD-1 and CTLA-4 are required for maintenance of non-immunogenic mRNA induced antigen-specific tolerance. EAE was actively induced by immunization with MOG35-55-CFA (day 0) and Pertussis Toxin (day 0 and 2) in C57BL/6 mice and mice were treated at day 7 and day 10 after EAE induction with 20 μg non-immunogenic MOG35-55-coding mRNA or 20 μg non-immunogenic irrelevant mRNA (n=8 mice/group). mRNA treated mice were treated concomitantly with anti-PD-1 or anti-CTLA-4 blocking antibodies or corresponding IgG controls. EAE development was assessed by daily health monitoring. EAE area under curve (AUC) was used to determine statistical significance via one-way ANOVA and Tukey's multiple comparison test of the different disease development curves.

Figure 20:
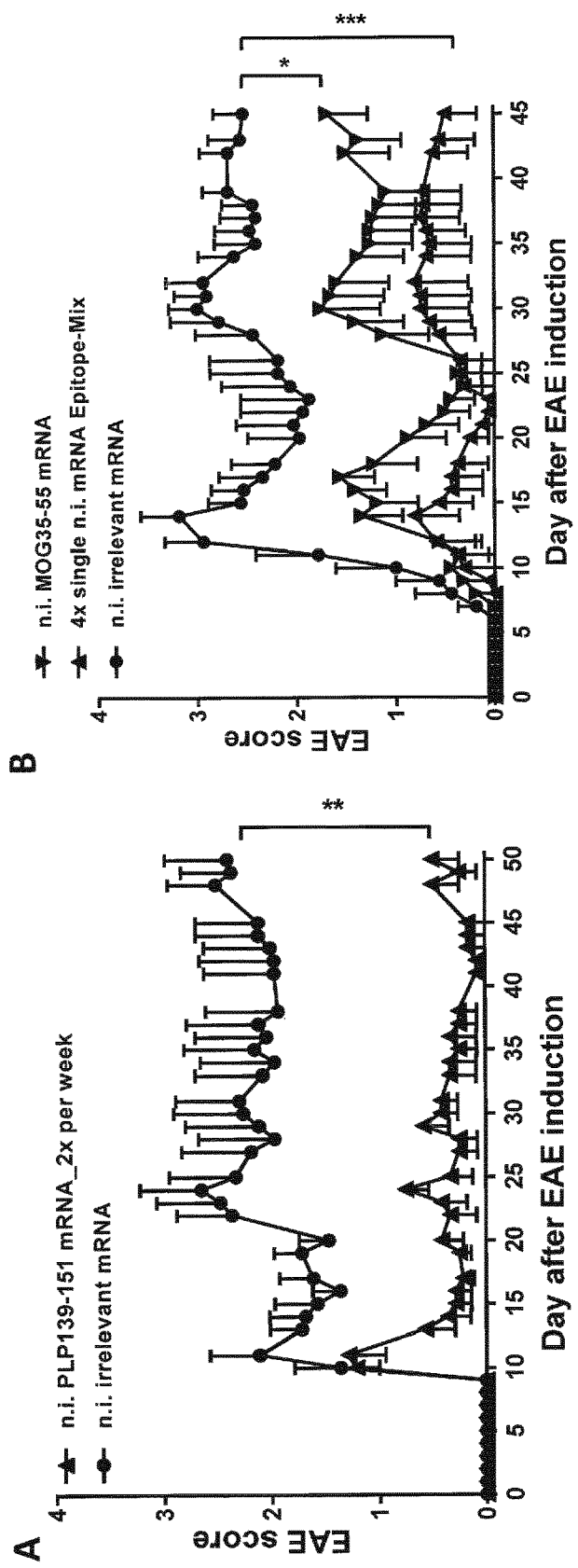

FIG. 20: Antigen-specific tolerance induction by treatment with non-immunogenic antigen-specific mRNA is independent of the EAE disease model. (A) Therapeutic vaccination with non-immunogenic PLP139-151 coding mRNA-LPX induces tolerance to relapsing-remitting EAE. EAE was actively induced by immunization with PLP139-151-CFA (day 0) and Pertussis Toxin (day 0 and 2) in SJL mice. 20 μg non-immunogenic PLP139-151 coding mRNA as well as non-immunogenic irrelevant mRNA were injected i.v. into the retro-orbital plexus 2× per week starting from day 7 and day 10 after EAE induction. (B) Therapeutic vaccination with non-immunogenic multi-epitope coding mRNA-LPX induces tolerance in a complex EAE. EAE was actively induced by immunization with MOG35-55, PLP139-151, PLP178-191, MBP84-104 and MOBP15-36-CFA (day 0) and Pertussis Toxin (day 0 and 2) in F1 hybride mice from C57BL/6 and SJL/JRj. 40 µg non-immunogenic multi-epitope coding mRNA, 20 µg non-immunogenic MOG35-55 mRNA and 20 µg non-immunogenic irrelevant mRNA were injected i.v. into the retro-orbital plexus 2× per week starting from day 7 and day 10 after EAE induction. EAE development was assessed by daily health monitoring. Data are depicted as mean. n=6-8 mice/group. EAE area under curve (AUC) was used to determine statistical significance via one-way ANOVA and Tukey's multiple comparison test of the different disease development curves.

Figure 21:
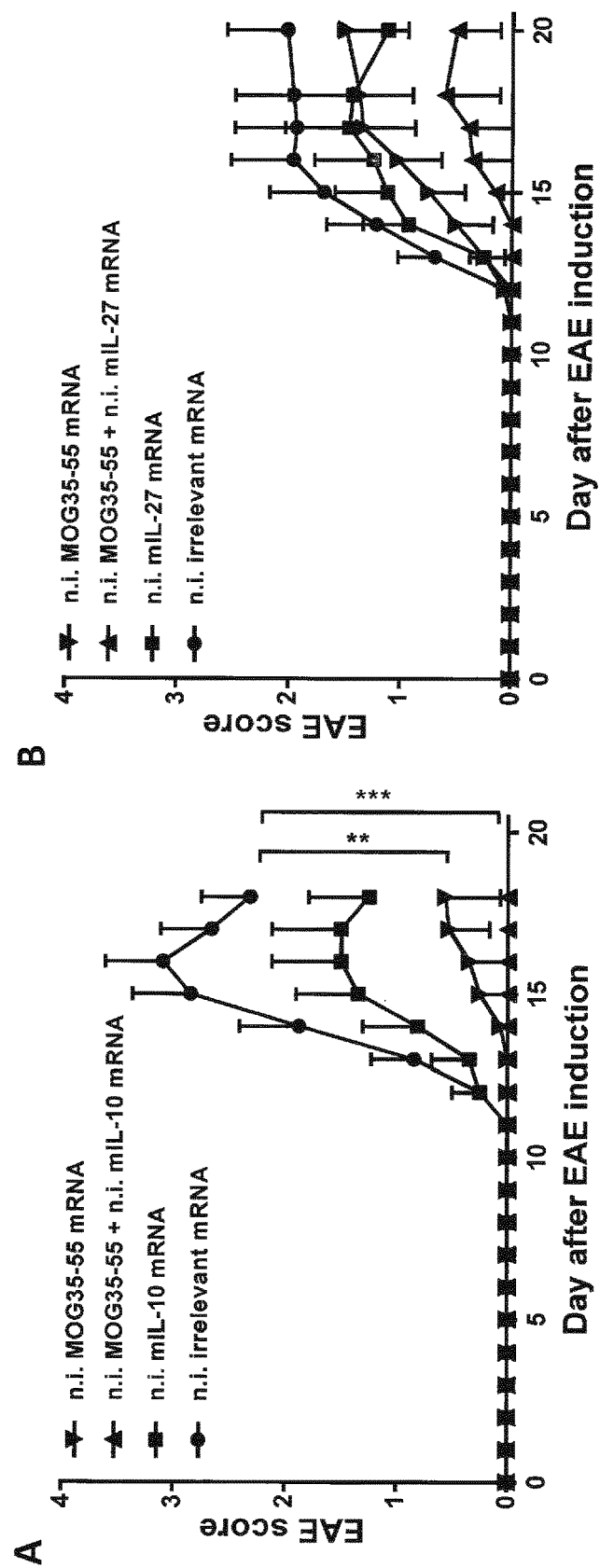

FIG. 21: Cytokine co-delivery by non-immunogenic mRNA improves the tolerogenic potency of non-immunogenic antigen-specific mRNA-LPX treatment in EAE model. EAE was actively induced by immunization with MOG35-55-CFA (day 0) and Pertussis Toxin (day 0 and 2) in C57BL/6 mice and mice were treated at day 7 and day 10 after EAE induction with 5 µg non-immunogenic MOG35-55 mRNA together with 15 µg non-immunogenic mIL-10 (A) or mIL-27 (B) mRNA, respectively. Control mice received 5 µg non-immunogenic MOG35-55 mRNA together with 15 µg non-immunogenic irrelevant mRNA, 15 µg non-immunogenic cytokine-coding mRNA or 20 µg non-immunogenic irrelevant mRNA. EAE development was assessed by daily health monitoring. Data are depicted as mean. n=6-8 mice/group. EAE area under curve (AUC) was used to determine statistical significance via one-way ANOVA and Tukey's multiple comparison test of the different disease development curves.

EXAMPLES

Example 1: Material and Methods

Animals

C57BL/6, BALB/c, SJL/JRj wild-type mice and F1 hibrid mice from C57BL/6 and SJL/JRj were purchased from ENVIGO RMS gmbH, Netherlands and Janvier Laboratories, France respectively. Thy1.1+ 2D2 TCR MOG transgenic C57BL/6 mice, expressing a T cell receptor recognizing MOG35-55 in the context of MHC class II (I-A$^b$), as well as Thy1.1+ 2D2 Foxp3-eGFP TCR MOG transgenic C57BL/6 mice that additionally include the knock-in Foxp3-eGFP, were kindly provided by the laboratory of Prof. Dr. Ari Waisman. Age and sex matched animals were used throughout the experiments and mice were maintained under specific pathogen-free (SPF) conditions at the animal facility of BioNTech AG Mainz.

RNA Constructs and In Vitro Transcription

In vitro transcription of LUC-mRNA were based on the pST1-hAg-CDS-FI-A30LA70 plasmid-backbone, which contains a 5' human alpha globin UTR (hAg), a 3' FI element and a poly(A) tail of 100 nucleotides, with a linker after 30 nucleotides. The LUC-construct contains the firefly luciferase gene. The MOG35-55, PLP139-151, PLP178-191 and MBP84-104 constructs were designed based on the same plasmid-backbone (pST1-hAg-CDS-FI-A30LA70) and additionally contained a mmsec(opt) and mmMITD(opt) sequence before and after the MOG35-55, PLP139-151, PLP178-191 and MBP84-104 coding sequences (pST1-hAg-mmsec(opt)-CDS-mmMITD(opt)-A30LA70), respectively. The addition of a leader peptide and a MHC trafficking signal (MITD) strongly improves antigen presentation by APCs (Kreiter, S. et al., 2007, J. Immunol. 180, 309-318). All antigen-sequences contain additionally seven flanking amino acids before and after the disease relevant epitope to facilitate antigen presentation. The antigen-sequence Myelin Oligodendrocyte Glycoprotein (MOG) has the peptide-sequence: MOG27-63: SPGKNATGMEVGWYR-SPFSRVVHLYRNGKDQDAEAQP (SEQ ID NO: 1). For the mouse myelin peptide Proteolipid Protein PLP139-151 also seven flanking amino acids were added for better peptide presentation (PLP131-159: AHSLERVCHCLGKWLGHPDKFVGITYALT; SEQ ID NO: 3). The Proteolipid Protein PLP178-191 includes the amino acids PLP170-199: AVPVYIYFNTWITCQ-SIAFPSKTSASIGSL (SEQ ID NO: 4) and the Myelin basic protein (MBP) 84-104 includes the amino acids MBP76-112: RTQDENPVVHFFKNIVTPRTPPPSQGKGR-GLSLSRFS (SEQ ID NO: 5). For control immunization with mRNA, empty vector was used, coding for no specific antigen-sequence (pST2-hAg-mmsec(opt)-emtpy-mm-MITD(opt)-2hBg-A30LA70). Cytokine coding mRNAs for murine Interleukine 10 (mIL-10) and murine Interleukine 27 (mIL-27) were also synthesized based on the plasmid-backbone pST1-hAg-CDS-FI-A30LA70. RNA was generated by in vitro transcription as described by Kreiter et al., 2007 (Cancer Immunol. Immunother. 56, 1577-87). Purified mRNA was eluted in $H_2O$ and stored at −80° C. until further use. In vitro transcription of all described mRNA constructs was carried out by BioNTech RNA Pharmaceuticals GmbH.

Generation of Non-Immunogenic mRNA

To generate the non-immunogenic mRNA used, 1-methyl-pseudouridin was used during in vitro transcription instead of the normal nucleoside Uridin, and mRNA was further purified by HPLC or Cellulose treatment. For HPLC purification the protocol of Weissman et al., 2013 (Methods Mol Bio. 969, 43-43), was adapted and elution of the mRNA was performed with a gradient of 38%-70% of Buffer B. From all generated mRNAs quality controls were performed (Bioanalyser and Dot-Blot analysis) to ensure the purity and integrity of the mRNA.

To generate the immunogenic mRNA used, the normal nucleoside Uridin was used for in vitro transcription and mRNA was not further purified by HPLC or Cellulose treatment.

For investigating the influence of HPLC-purification or Cellulose-treatment on the activation of splenocytes, pseudouridine-modified mRNA (pU-mRNA) was used, that either received an additional HPLC purification (pU-HPLC mRNA) or not. The corresponding mRNA was generated as already described.

Dotblot-Analysis for Quality Control of IVT mRNA

In vitro transcribed, modified and HPLC-purified mRNA was analyzed for double-stranded mRNA (dsRNA) by Dot-blot. 1 µg of different mRNA constructs were loaded on a NYTRAN SPC membrane (GE Healthcare), blocked and then incubated with J2 antibody (SCICONS English and Scientific Consulting) for the detection of dsRNA. As secondary antibody anti-mouse HRP antibody (Jackson ImmunoResearch) was used and membranes were analyzed with a BioRad ChemiDoc.

Preparation and Injection of RNA-Lipoplexes

RNA-lipoplexes (RNA-LPX) were prepared under sterile and RNase-free conditions. HEPES (10 mM)/EDTA (0.1 mM) was used to dilute the RNA to a concentration of 1 mg/ml. 1.5 M NaCl (5 M NaCl Stock; Ambion) were added to a specific volume of RNA to obtain a final concentration of 150 mM NaCl. After briefly vortexing, a specified volume of F12 liposomes was added and the RNA-liposome mixture (RNA-LPX) was again briefly vortexed and finally incubated for 10 min at RT to enable the formation of RNA-LPX (Kranz et al. 2016, Nature. 16, 396-401). 200 µl RNA-LPX solution was injected per mouse intravenously into the retro-orbital plexus of the mice.

Flow Cytometric Analysis

Fluorescence-activated cell sorting (FACS) surface and intracellular antibodies were purchased from eBioscience or BD Pharmingen and used in accordance with the manufacturer's protocol. Antibodies used were the following: CD11b, CD11c, CD19, CD25, CD4, CD44, CD40L, CD49b, CD69, CD8, CD86, CD90.1, Foxp3. ICOS, IFNγ, IL-17A, Lag-3, PD-1, TIGIT and Tim-3.

Single cell suspensions from different organs were stained for 30 min at 4° C. for extracellular markers. For intracellular cytokine staining of IFNγ, IL-17A and CD40L, cells were isolated as described and additionally stimulated in culture medium containing MOG35-55 peptide (conc. 15 µg/ml), Monensin (GolgiStop, BD-Bioscience) and Brefeldin A at 37° C., 5% $CO_2$ for 6 h. After performing live-dead staining (viability dye eFluor® 506, eBioscience) and staining of cell-surface markers, cells were fixed and permeabilized using Cytofix/Cytoperm and Perm/Wash buffer from BD Biosciences in accordance to the manufacturer's protocol. Cells were incubated for 30 min at 4° C. with intracellular antibodies and washed twice in Perm/Wash before FACS analysis. Samples were acquired on a BD LSR Fortessa or BD FACS Canto II and analyzed using FlowJo 7.6.5 or FlowJo 10.4 (Tree Star) software.

For intracellular Foxp3 staining the Foxp3 transcription factor staining buffer set (Thermo Fisher Scientific) was used for fixation and permeabilization. All steps were performed according to the manufacturer's recommendation after extracellular staining.

MOG35-55 specific $CD4^+$ T cells were detected by tetramer staining. MOG35-55 specific APC-conjugated pMHC class II tetramer was obtained from the National Institutes of Health Tetramer Core Facility. Single cell suspensions of mouse splenocytes were incubated with MOG35-55 APC-conjugated tetramer for 1 h at room temperature in complete DC medium (for media composition see "Generation of bone marrow-derived DCs (BMDCs)"). Cells were washed and anti-APC staining and subsequent MACS were performed. Cells were incubated with extracellular or intracellular antibodies as described above.

For determination of absolute $CD4^+$ MOG35-55 specific cell counts ($Thy1.1^+$ 2D2 $CD4^+$ T cells) in the spleen, brain and spinal cord, Trucount™ Tubes (BD Biosciences) were used. Single cell suspensions were stained as described above, subsequently transferred into Trucount™ tubes and absolute cell counts were determined by flow cytometry.

In Vivo Bioluminescence Imaging (BLI)

Translation efficiency of non-immunogenic mRNA in spleen cells was investigated using Xenogen IVIS Spectrum in vivo imaging system (Caliper Life Sciences). 6 h, 24 h, 48 h and 72 h after RNA-LPX-immunization of non-immunogenic LUC-mRNA, mice were injected i.p. with an aqueous solution of D-luciferin (250 µl, 1.6 mg in PBS) (BD Biosciences). After 5 minutes, signal intensities from the spleen were defined and measured by in vivo bioluminescence in regions of interest (ROI) and quantified as total flux (photons/sec) using IVIS Living Image 4.0 Software. The acquisition time was 1 min at binning 4. During bioluminescent imaging of the live mice, mice were anesthetized with a dose of 2.5% isoflurane/oxygen mixture. The LUC signal intensity of emitted photons of live animals was depicted as a grayscale image, where black is the least intense and white the most intense bioluminescence signal. Images of mice were analyzed using the IVIS Living Image Software.

Magnetic Activated Cell Sorting (MACS)

$Thy1.1^+$ 2D2 $CD4^+$ T cells of $Thy1.1^+$ 2D2 TCR MOG transgenic C57BL/6 mice or $Thy1.1^+$ 2D2 Foxp3-eGFP TCR MOG transgenic C57BL/6 mice, were isolated from spleen and lymph node by positive selection using MACS (Miltenyi Biotec) according to the manufacturer's instruction. $CD4^+$ T cells were purified using CD4 (L3T4) Micro Beads.

$CD4^+$ MOG35-55 specific T cells were MACS-enriched after MOG35-55 specific APC-conjugated pMHC class II tetramer staining using anti-APC Micro Beads. Enrichment was performed according to the manufacturer's protocol.

Generation of Bone Marrow-Derived DCs (BMDCs)

Bone marrow (BM) cells were extracted from femur and tibia of C57BL/6 mice and cultured in tissue culture flasks at 37° C. in RPMI 1640+GlutaMAX-I medium (Gibco) supplemented with 10% FBS (Biochrom), 1% Sodium Pyruvate 100× (Gibco), 1% MEM NEAA 100× (Gibco), 0.5% penicillin-streptomycin (Gibco), 50 µM 2-Mercaptoethanol (Life Technologies) and 1000 U/ml dendritic cell (DC) differentiation factor granulocyte-macrophage colony-stimulation factor (GM-CSF) (Peprotech). At day 6, 2×106 DCs/ml were pre-incubated for 3 h at 37° C. with MOG35-55 peptide (15 µg/ml) and then co-cultured with T cells in a total volume of 200 µl medium in a 96-well plate.

In Vitro Treg Suppression Assay

For in vitro Treg suppression studies, CTV-labeled (Cell-Trace Violet cell proliferation kit, Thermo Fisher Scientific) naïve $CD4^+$ 2D2 transgenic ($Thy1.1^+$) T cells ($3×10^4$ cells per well) were co-culture with isolated and CFSE labeled (5 µM) $CD4^+$ 2D2-Foxp3-eGFP transgenic cells of repetitively mRNA immunized mice in different ratios of suppressor and responder 2D2 T cells (1:1, 2:1, 4:1, 8:1). The 2D2-Foxp3-eGFP mice were injected intravenously into the retro-orbital plexus at day 0, day 3, day 6 and day 9 with non-immunogenic and immunogenic MOG35-55 mRNA as well as non-immunogenic irrelevant mRNA and saline. The proliferation of CTV-labeled responder 2D2 T cells was analyzed by flow cytometry 72 h after restimulation with MOG35-55 peptide-loaded BMDCs (final concentration 15 µg/ml MOG35-55 peptide).

Adoptive T Cell Transfer and In Vivo Proliferation Assay

For proliferation studies, enriched $CD4^+$ 2D2 transgenic (Thy1.1V) T cells were CTV-labeled (CellTrace Violet cell proliferation kit, Thermo Fisher Scientific) according to the manufacturer's instruction, counted and $7×10^6$ cells injected i.v. into the retro-orbital plexus in 200 µl PBS into naïve C57BL/6 ($Thy1.2^+$) recipient mice under anesthesia. At the next day C57BL/6 mice were immunized with 10, 20 or 40 µg of non-immunogenic mRNA coding for the MOG35-55 epitope. Control mice received either 20 µg of non-immunogenic irrelevant mRNA or saline. 4 days after T cell transfer, mice were sacrificed and cells were analyzed for proliferation by flow cytometry.

For determination of absolute cell counts of $CD4^+$ MOG35-55 specific T cells in the spleen, brain and spinal cord as well as phenotypic analysis of these cells after successful mRNA treatment at day 7 and day 10 of EAE mice, $CD4^+$ 2D2 transgenic (Thy1.1+) T cells were isolated from $Thy1.1^+$2D2 TCR MOG transgenic C57BL/6 mice, enriched for CD4 cells by MACS and $7-10×10^6$ cells in 200 µl PBS were injected i.v. into the retro-orbital plexus into naïve C57BL/6 ($Thy1.2^+$) recipient mice under anesthesia using an oxygen-isoflurane vaporizer (2.5% isoflurane/oxygen). On the day after, EAE was actively induced in C57BL/6 mice.

ELISA

Detection of mouse IFN-α was performed by ELISA (PBL) 6 hours after RNA-immunization in mouse sera using standard ELISA assay according to manufacturer's instructions.

Th1/Th2/Th9/Th17/Th22 and Treg cytokines present in cell culture supernatants of restimulated splenocytes of repetitively mRNA treated mice were quantified using a 17-plex mouse ELISA assay kit (Thermo Fisher Scientific). Single cell suspensions of splenocytes ($5 \times 10^5$ cells) isolated from mice were stimulated for 72 h with 0, 5, 10, 20 or 100 µg/ml of MOG35-55 peptide, and supernatants were analyzed for cytokine content.

IFNγ Enzyme-Linked Immune Spot Assay (ELISpot)

Frequencies of MOG35-55 responding T cells were examined by Interferon γ (IFNγ) ELISpot. Mice were treated at day 0, 3, 7 and 10 with non-immunogenic MOG35-55 mRNA, non-immunogenic irrelevant mRNA or saline. At day 13 after first treatment, spleens of different treatment groups were isolated and single cell suspensions were prepared. $CD4^+$ T cells were purified by MACS using CD4 (L3T4) Micro Beads. Quantification of IFNγ responding antigen-specific T cells was performed upon restimulation with MOG35-55 peptide using the ELISpot kit. 96-well ELISpot plates (MultiScreenHTS IP Filter Plate, Merck Millipore) were coated over night with IFNγ-specific capture antibody (anti-mouse IFNγ antibody, Mabtech). After blocking with complete medium, plates were washed and $5 \times 10^5$ $CD4^+$ T cells were plated together with $1 \times 10^5$ MOG35-55 peptide-loaded BMDCs (peptide-concentration 15 µg/ml). As a control, $CD4^+$ T cells were incubated with irrelevant peptide-loaded BMDCs. All cells were cultured for 16 h in a 37° C., 5% $CO_2$ humidified incubator. Cells were washed and incubated for 2 h at 37° C. and 5% $CO_2$ with the biotinylated anti-IFNγ detection antibody (anti-mouse IFNγ biotinylated antibody, Mabtech). This secondary antibody was visualized by adding ExtrAvidin-Alkaline phosphatase (Sigma) and after incubation for 1 h, BCIP/NBT liquid substrate (Sigma) was added and the reaction was stopped after 1-3 min by rinsing the plate under running tab water. Quantification of spots was performed on an ELISpot Reader (S6 Macro Analyzer: CTL).

Induction of EAE and Treatment of Mice with mRNA

EAE was actively induced in eight- to ten-week old female C57BL/6 mice with 50 µg of MOG35-55 peptide (amino acid sequence: MEVGWYRSPFSRVVHLYRNGK; SEQ ID NO: 2) emulsified in CFA (Difco Laboratories) supplemented with 10 mg/ml of heat-inactivated *Mycobacterium tuberculosis* H37RA (Difco Laboratories) subcutaneously (s.c.) at the base of the tail. The mice received 150 ng of Pertussis toxin (List Biological Laboratories, INC., Campbell, Calif.) intraperitoneally (i.p.) on the day of immunization and 2 days later. Mice were weighted and scored daily starting on day 10 after immunization according to the following criteria: 0, no disease; 1, decreased tail tone; 2, impaired righting reflex; 3, partial hind limb paralysis; 4, complete hind limb paralysis; 5, hind limb paralysis with partial fore limb paralysis; and 6, moribund or dead.

EAE was furthermore actively induced in female SJL/JRj mice (8-10 weeks) with 200 µg of PLP139-151 peptide (amino acid sequence: HSLGKWLGHPDKF; SEQ ID NO: 6) emulsified in CFA supplemented with 10 mg/ml of heat-inactivated *Mycobacterium tuberculosis* H37RA s.c. at the base of the tail. The mice received 200 ng PTX i.p. on the day of immunization and 2 days later. Mice were weighed and scored daily starting on day 8 after immunization according to the already described scoring criteria.

A complex EAE was actively induced in female F1 hybrid mice from C57BL/6 and SJL/JRj (8-10 weeks) with 250 µg of peptide mixtures (MOG35-55, PLP139-151, PLP178-191 (amino acid sequence: NTWTTCQSIAFPSK; SEQ ID NO: 7), MBP84-104 (amino acid sequence: VHFFKNIVTPRTPPPSQGKGR; SEQ ID NO: 8), MOBP15-36 (amino acid sequence: QKFSEHFSIHCCPPFTFLNSKR; SEQ ID NO: 9)). Of each peptide 50 µg were used. The peptide mixture was emulsified in CFA supplemented with 10 mg/ml of heat-inactivated *Mycobacterium tuberculosis* H37RA and injected s.c. at the base of the tail. The mice received 200 ng PTX i.p. on the day of immunization and 2 days later. Mice were weighed and scored daily starting on day 8 after immunization according to the already described scoring criteria.

To determine protective immunity in C57BL/6 mice, mice were treated on day 7 and day 10 or at an EAE score of 1-2 after disease induction with 20 µg non-immunogenic MOG35-55 coding, 20 µg non-immunogenic irrelevant control mRNA or saline.

Therapeutic treatment of relapsing-remitting EAE in SJL mice was performed with 20 µg non-immunogenic PLP139-151 mRNA 2× per week starting from day 7 and day 10 after EAE induction. Control mice received 20 µg non-immunogenic irrelevant control mRNA.

In experiments comparing non-immunogenic single-epitope mRNA treatment with non-immunogenic multi-epitope treatment, complex EAE mice were treated with 40 µg non-immunogenic multi-epitope coding mRNA (10 µg of each non-immunogenic epitope-coding mRNA (MOG35-55, PLP139-151, PLP178-191, MBP84-104) was used), 20 µg non-immunogenic MOG35-55 mRNA or 20 µg non-immunogenic irrelevant control mRNA. mRNA was injected 2× per week starting from day 7 and day 10 after EAE induction.

For testing combinatorial effects of cytokine coding mRNA and antigen-specific mRNA treatment, 5 µg non-immunogenic MOG35-55 coding mRNA were injected together with 15 µg non-immunogenic mIL-10 or mIL-27 coding mRNA on day 7 and day 10 after EAE induction. Control mice received 5 µg non-immunogenic MOG35-55 mRNA together with 15 µg non-immunogenic irrelevant mRNA, 15 µg non-immunogenic cytokine-coding mRNA or 20 µg non-immunogenic irrelevant mRNA.

For all experiments mRNA was injected i.v. into the retro-orbital plexus under anesthesia using an oxygen-isoflurane vaporizer (2.5% isoflurane/oxygen).

Antibody Treatment

C57BL/6 mice were treated with PD-1 (500 µg first treatment, 250 µg following treatments, clone RMP1-14, BioXcell), or CTLA-4 (500 µg first treatment, 250 µg following treatments, clone 9H10, BioXcell) blocking antibody or isotype-matched control antibodies (Rat IgG2a and syrian hamster IgG, BioXCell) on day 7, 10, 14 and 17 after EAE induction. Antibodies were diluted in PBS and applied i.p.

Isolation of Splenic, LN and CNS Infiltrates

All cell-based analyses were performed on single cell suspension of spleen, lymph node and CNS organs. In brief, spleens and LNs were incubated with 1 mg/ml collagenase D and 0.1 mg/ml DNaseI for 15 min and then mashed through a 70 µm cell strainer while rinsing with PBS. Erythrocyte lysis (hypotonic lysis buffer: 1 g $KHCO_3$ and 8.25 g $NH_4Cl$ dissolved in 1 l $H_2O$ and 200 µl 0.5 M EDTA)

was performed on single cell suspension of splenocytes. After an additional washing step with PBS, cells were counted with the Vi-Cell cell counter (Beckman Coulter).

For isolation of CNS infiltrates from brain and spinal cord, mice were anesthetized with Ketamine-Rompun and perfused using 0.9% NaCl through the heart left ventricle. The brain and spinal cord were removed manually, cut into small pieces and digested in PBS++ (PBS with calcium and magnesium, Gibco) containing collagenase D (1 mg/ml) and DNase I (0.1 mg/ml) for 20 min at 37° C. The digested tissue was then homogenized manually by sucking up the tissue pieces into a syringe and pressing out again against the wall of a 15 ml falcon tube. This was performed up to 10 times, until no pieces were visible. The single cell suspension was resuspended in 70% Percoll and layered under a 30:37 Percoll gradient. The final Percoll gradient was 30:37:70% and was centrifuged at 300 g for 40 min at room temperature. The mononuclear cell layer lying at the interphase between 70% and 37% Percoll was washed with 2% FCS/PBS before further analyses.

Statistical Analysis

Statistical significance was evaluated using GraphPad Prism 7 software (Graphpad Software, Inc.) employing one-way ANOVA corrected with Tukey's-comparison test factor when more than two groups were compared. EAE development curves were compared by calculating the area under the disease development curve (AUC) for single mice. Values of $p \leq 0.05$ were considered to be statistically significant; $*p \leq 0.05$, $p \leq 0.01$, $*p \leq 0.001$, $****p \leq 0.0001$. The employed tests are referred to in the respective figure legends.

Example 2: Examination of Non-Immunogenic mRNA Regarding Activation of Splenocytes In order to analyze the activation of splenocytes and translation efficiency of the used non-immunogenic mRNA, BALB/c mice were injected intravenously into the retro-orbital plexus with Luciferase-mRNA (10 µg) complexed with F12 liposomes. Luciferase activities were assessed via in vivo imaging 6, 24, 48 and 72 hours after RNA-LPX injection and representative mice are shown in FIG. 1C. Immunization of mice with non-immunogenic mRNA led to a lasting high translation of the LUC-mRNA. Consequently LUC protein expression could be detected up to 72 hours after mRNA immunization.

Furthermore, as seen in FIG. 1A, immunization of mice with non-immunogenic mRNA led to no upregulation of activation markers CD86 on DCs and CD69 on lymphocytes like in untreated control mice. In mice immunized with non-immunogenic LUC-mRNA also no IFNα could be detected in the blood 6 hours after mRNA immunization (FIG. 1B).

Example 3: Characterization of Non-Immunogenic mRNA

Non-immunogenic mRNA is used to deliver specific disease relevant antigens to dendritic cells to ensure antigen-presentation without immune activation in therapeutic applications. It has been shown that the incorporation of 1-methylpseudouridine into mRNA enhances the protein expression in the cells and reduces the immunogenicity of the mRNA in mammalian cell lines as well as in vivo in mice (Andries et al., 2015, J Control Release. 217, 337-344). This effect relies most likely on the increased ability of the mRNA to evade activation of endosomal Toll-like receptors and downstream innate immune signaling (Andries et al., 2015). Additionally to the use of 1-methylpseudouridine instead of the nucleoside uridine for the incorporation into the mRNA during in vitro transcription, HPLC purification of the synthetic mRNA eliminates furthermore immune activation and improves the translation of the nucleoside-modified, protein-encoding mRNA (Kariko et al., 2011, Nucleic Acids Res. 39, e142). By HPLC purification remaining double-stranded mRNA contaminants are removed after mRNA in vitro transcription, resulting in mRNA that does not induce Interferon signaling and inflammatory cytokines (Kariko et al., 2011). An alternative method for the purification of the nucleoside-purified mRNA is the Cellulose-purification (PCT/EP2016/059056).

To investigate whether the mRNA used for therapeutic application is really non-immunogenic, Bioanalyzer and Dotblot analysis were performed to ensure the integrity and the purity of the mRNA. FIG. 2 shows Dotblot analysis of non-immunogenic MOG35-55 mRNA purified by either Cellulose treatment or HPLC purification. The J2 antibody, specific for dsRNA, showed no signal after Cellulose or HPLC purification of the analyzed MOG35-55 mRNA in a range of 40 ng up to 1 µg of used mRNA. This quality control ensures non-immunogenic mRNA characteristics as for both mRNA batches, positive therapeutic effects could be achieved in the EAE treatment. EAE was actively induced in C57BL/6 mice and mice were treated at day 7 and day 10 after disease induction with antigen-specific MOG35-55 coding non-immunogenic mRNA purified either by Cellulose or HPLC method. Both groups were completely resistant to EAE induction (FIG. 3). More detailed description about therapeutic vaccination with non-immunogenic antigen-specific mRNA will be explained in the following examples.

Example 4: Effects of Immunization of Non-Immunogenic MOG35-55 mRNA on the Proliferation of Antigen-Specific T Cells To study whether the immunization of non-immunogenic MOG35-55 mRNA-LPX results in the presentation of MOG35-55 antigen by DCs to T cells, the proliferation of antigen-specific CD4$^+$ T cells (CD4$^+$ 2D2 T cells) that harbor the myelin oligodendrocyte glycoprotein (MOG)-specific T cell receptor, was investigated. Cell-Trace-Violet (CTV)-labeled Thy1.1V MOG35-55-specific CD4$^+$ 2D2 T cells were transferred into Thy1.2$^+$ C57BL/6 mice. 24 hours later the recipient mice were immunized with different concentrations (10, 20 or 40 µg of mRNA) of non-immunogenic mRNA coding for the MOG35-55 epitope and another 4 days later the MOG35-55-specific CD4$^+$ 2D2 T cells were analyzed for proliferation. Control mice received either 20 µg of non-immunogenic irrelevant mRNA or saline. 2D2 T cells proliferated when mice were treated with non-immunogenic MOG35-55 mRNAs in comparison to the control mice (FIG. 4), indicating that antigen presenting cells (APCs) translate and process the antigen-coding non-immunogenic mRNA in the correct manner and present the MOG35-55 peptide. Furthermore immunization of mice with non-immunogenic MOG35-55 mRNA with increasing doses from 10 to 40 µg showed also an increase in the antigen-specific T cell population.

Example 5: Immunization with Antigen-Specific Non-Immunogenic mRNA Induces the Development of Regulatory T Cells in Naïve Mice Tregs are fundamental in controlling various immune responses and they are important for tolerance induction and maintenance. Preclinical studies in animal models show that adoptive transfer of Tregs can prevent or cure several T cell-mediated diseases, including autoimmune diseases, by restoring immune tolerance to self antigens. Several CD4+ regulatory T cells have been described (Shevach, E. M., 2006, *Immunity* 25, 195-201) and categorized into two major subgroups: natural and inducible Tregs, which are generated in the periphery under various tolerogenic conditions. Treg cells regulate the priming of autoreactive T cells by limiting their expansion and differentiation (Sakaguchi, S. et al., 2008, Cell 133, 775-87).

To further investigate the effects of immunization with antigen-specific non-immunogenic mRNA on the corresponding T cell phenotype, a 2D2-Foxp3-eGFP fusion protein has been transfected into the T cells of Th1.1 positive mice. These mice were repetitively immunized (d0, d3, d6 and d9) with non-immunogenic and immunogenic MOG35-55 mRNA, as well as non-immunogenic irrelevant mRNA or saline. Immunization of the mice with non-immunogenic MOG35-55 mRNA led to the development of Foxp3+ cells in the mice, analyzed 4 days after the last mRNA treatment (d13). Mice treated with immunogenic antigen-specific mRNA or irrelevant non-immunogenic mRNA showed no increase in Foxp3 cell population and had a frequency of Foxp3 positive cells like the saline treated control mice (FIGS. 5A and B).

Whether the induced Foxp3+ cells act suppressive was assessed by an in vitro suppression assay (FIG. 5C). Therefore, total CD4+ cells of immunized mice were labeled with CFSE and co-cultured for 72 hours in different suppressor to responder ratios with naïve MOG35-55-specific CD4+ 2D2 T cells that were additionally labeled with CTV. Importantly, induced regulatory cells from mice immunized with non-immunogenic MOG35-55 mRNA mediated a dose-dependent suppression of the 2D2 effector T cell proliferation in presence of MOG35-55 peptide-loaded BMDCs. In contrast, all other groups exerted no suppressive activity.

Taken together, these results indicate that APC-specific antigen presentation under non-inflammatory conditions mediated the development of functional regulatory T cells.

Example 6: Influence of Therapeutic Vaccination with Non-Immunogenic MOG35-55 mRNA in the Disease Model EAE To elucidate the tolerogenic effect of mRNA immunization with antigen-specific non-immunogenic mRNA in a disease model, EAE was actively induced in C57BL/6 mice and mice were treated at day 7 and day 10 after disease induction with antigen-specific MOG35-55 coding non-immunogenic mRNA, as well as non-immunogenic irrelevant mRNA. The treatment was started at a time point at which strong DC activation and maturation signals as well as the first T cell priming had already taken place. RNA-immunization with non-immunogenic antigen-specific mRNA completely blocked any signs of EAE (FIG. 6) and no single mouse out of 6 mRNA immunized mice developed the disease.

At the same time, treatment of mice with non-immunogenic mRNA coding for an irrelevant epitope, did not protect the mice from the disease and 5/6 mice developed an EAE (FIG. 6). These findings show that MOG presentation by immature DCs can downmodulate EAE and only animals treated with non-immunogenic antigen-specific mRNA are completely resistant to EAE induction.

Furthermore, it was investigated whether EAE can be treated during later time points of disease progression, when symptoms of the disease are visible and mice reached a disease score of 1-2. Remarkably, it could be shown that after RNA-immunization with non-immunogenic MOG35-55-coding mRNA EAE mice did not develop a severe EAE and the symptoms could be reduced when treated at score 1 (FIG. 7). Even when mice were treated at a score of 2 a fast disease progression could be stopped. The mice only showed a maximal disease score of 2-3, whereas nearly all untreated control mice developed a full EAE with a maximal score of 4. In comparison to EAE mice treated with non-immunogenic MOG35-55 coding mRNA, therapeutic treatment with non-immunogenic irrelevant mRNA had no positive effect on the disease progression and the animals developed EAE similar to the untreated control mice.

To study the molecular mechanism of mRNA-treatment induced tolerance and to see whether the mRNA-immunization with non-immunogenic antigen-specific mRNA and thereby the presentation of MOG35-55 by DCs directly influences effector T cells (Teff), EAE was again induced in C57BL/6 mice, animals were treated with non-immunogenic MOG35-55-coding mRNA at day 7 and day 10 after disease induction and 6 days after the last mRNA-treatment spleen, LN, brain and spinal cord were isolated. Cells from the different organs were reactivated in vitro with MOG35-55 peptide for 6 hours and then gated on CD40 ligand (CD40L) Teff cells. CD40L is rapidly expressed on T cells after activation and was therefore used as a marker for MOG-specific Teff cells. As seen in FIG. 8, administration of non-immunogenic MOG35-55 mRNA leads to significant decrease in the frequency of antigen-specific CD4+ T cells in the groups treated with non-immunogenic antigen-specific mRNA in brain and spinal cord. On the functional level it could be shown that CD4+ T cells secrete significantly less Interferon-γ (IFNγ) in the brain and Interleukin-17A (IL-17A) in the spinal cord in mice treated with non-immunogenic MOG35-55 coding mRNA compared to untreated control mice (FIG. 9). These data indicate that mRNA-treatment with non-immunogenic MOG35-55 mRNA can inactivate memory T and Teff cells, leading to a reduction of these cells.

Example 7: Influence of mRNA-Purity on the Treatment-Efficiency of EAE

Experiments with combinations of immunogenic mRNA containing uridine (U) and non-immunogenic mRNA containing 1-methylpseudouridine and being purified by cellulose purification (m1Y) revealed that activation of splenocytes (examined by upregulation of the activation marker CD86 on DCs and CD69 on lymphocytes) as well as IFNα secretion correlates with the amount of used immunogenic mRNA. Nearly no activation was achieved with non-immunogenic mRNA (20 μg m1Y MOG35-55 mRNA) and the activation increased steadily by addition of immunogenic mRNA (U MOG35-55 mRNA) (FIG. 10). 5 μg U mRNA+15 μg m1Y mRNA showed only slightly less activation than 20 μg U mRNA, whereas 20 μg m1Y mRNA again did not activate the immune system at all. Corresponding Dotblot analysis of the different mRNA mixtures also revealed that only 100% of non-immunogenic (m1Y) mRNA show no signal for dsRNA (FIG. 11).

To further investigate the influence of the purity of used mRNA on the treatment efficacy of EAE the same mRNA mixtures were used in order to treat an ongoing EAE. Again, EAE was actively induced in C57BL/6 mice and mice were treated at day 7 and day 10 after disease induction with antigen-specific mRNA. In this experiment the same mRNA mixtures of non-immunogenic and immunogenic MOG35-55 mRNA were used as in the previous "activation" experiment. Unlike 100% non-immunogenic (m1Y) mRNA, mixture of non-immunogenic and immunogenic mRNA (2.5 µg U+17.5 µg m1Y MOG35-55 mRNA as well as 5 µg U+15 µg m1Y MOG35-55 mRNA) cannot prevent the disease development completely and some mice start to develop the disease similar to mice treated with 100% immunogenic mRNA (FIG. 12). These results show that for an effective treatment of EAE pure non-immunogenic (m1Y) mRNA is necessary.

An additional comparison in terms of splenic activation of unmodified and modified mRNA, which was either or not purified by HPLC, was performed. As depicted in FIG. 13, nucleoside-modifications such as pseudouridine (pU) alone, does not induce a loss of recognition of the mRNA by the immune system, but the purification process makes the difference. Non-purified pU-mRNA is still immunogenic and it works like regular mRNA (U-mRNA) in terms of splenic activation (strong upregulation of CD86 on DCs, upregulation of CD69 on B cells, T cells and NK cells) and IFNα secretion. In contrast, pU-mRNA that was additionally purified by HPLC in order to get rid of dsRNA (pU-HPLC mRNA) prevents DC, B cell, T cell and NK cell activation and consequently the secretion of IFNα like in untreated control mice. These results underline that exclusively the combination of Uridine-modification and additional purification of the IVT mRNA minimizes the immunogenicity of the mRNA to zero as observed in naïve mice, a level where tolerance can be induced. Thus, non-immunogenic mRNA (uridine-modified in combination with mRNA-purification) is the optimal mRNA for the purpose of tolerance induction.

Example 8: Treatment with Non-Immunogenic MOG35-55-Specific mRNA does not Induce De Novo Priming of Antigen-Specific CD4$^+$ T Cells but Results in the Expansion of Anergic T Cells in Naïve Mice The maintenance and induction of peripheral tolerance is dependent on the presentation of self-antigen by APCs that express low levels of co-stimulatory molecules, like CD86 or CD40, on their surface. The absence of co-stimulatory-molecule expression and cytokine production by APCs upon treatment with non-immunogenic mRNA was shown in Example 2, FIG. 1. Consequently, upon mRNA treatment, APCs process and present the epitope encoded by the non-immunogenic mRNA in the absence of activating stimuli. TCR engagement in the absence of costimulatory signals does not result in the expansion of effector T cells, rather in apoptosis or T cell anergy (Mueller, D. L., 2010, Nat. Immunol. 11, 21-7). In contrast, during effector T cell priming, DCs release specific cytokines, which together with antigen presentation and the expression of costimulatory molecules polarize effector immune responses by driving the differentiation of CD4$^+$ T cells into Th1, Th2 or Th17 cells. Indeed, generation of effector T cells upon non-immunogenic antigen-specific mRNA treatment is not intended in an autoimmune disease, as more effector T cells might even lead to a more severe course of the disease instead of a curative treatment.

To investigate the generation of antigen directed T cell responses, naïve C57BL/6 mice were repetitively treated (day 0, 3, 7 and 10) with 20 µg non-immunogenic MOG35-55 coding mRNA, 20 µg non-immunogenic irrelevant mRNA or saline. After four mRNA immunizations, CD4$^+$ T cells were isolated on day 13 from the spleens and an IFNγ ELISpot was performed. FIG. 14A shows that mice treated with non-immunogenic MOG35-55 coding mRNA did not develop IFNγ$^+$ CD4$^+$ effect T cells responding to antigen-recognition upon antigen-specific mRNA treatment.

In accordance with these results, also restimulation of splenic CD4$^+$ T cells with different concentrations of MOG35-55 peptide (0, 5, 10, 20 and 100 µg) for 48 h did not result in the secretion of other inflammatory cytokines such as TNFα and GM-CSF, as measured in the supernatants by ELISA (FIG. 14B). Only the secretion of the anti-inflammatory cytokine IL-10 was detected in the mice treated with non-immunogenic antigen-specific mRNA, but not with non-immunogenic irrelevant mRNA (FIG. 14C). Furthermore, only in this group, the secretion of Th2 cytokines like IL-4 and IL-5 could be detected (data not shown). The production of IL-10 in response to non-immunogenic antigen-specific mRNA provides evidence of antigen-specific regulatory T cells (Tregs) being activated in response to the treatment Tregs are fundamental in controlling various immune responses. Many different subsets of inducible Tregs have been reported and especially CD25$^+$Foxp3$^+$ and Tr1 cells are characterized by the production of high levels of IL-10. These regulatory T cells regulate the priming of autoreactive T cells by limiting their expansion and differentiation.

To investigate the CD4 phenotype after non-immunogenic antigen-specific mRNA treatment, C57BL/6 mice were repetitively immunized with 20 µg non-immunogenic antigen-specific MOG35-55 mRNA, 20 µg non-immunogenic irrelevant mRNA or saline on day 0, 3, 7 and 10. The expression of TIGIT, Tim-3, PD-1 and Lag-3 on CD4$^+$ MOG35-55 tetramer$^+$ cells from mice treated with non-immunogenic MOG35-55 coding mRNA was compared to total CD4$^+$ cells of non-immunogenic irrelevant and untreated control mice. Repetitive immunization with non-immunogenic antigen-specific mRNA results in an upregulation of TIGIT, Tim-3, PD-1 and Lag-3 in comparison to mice treated with non-immunogenic irrelevant mRNA (FIG. 15).

The upregulation of these markers correlates with an anergic T cell phenotype. Anergy is an acquired state of functional unresponsiveness and the consequence of the engagement of the T cell receptor (TCR) without costimulation through CD28 (Jenkins, M. K. et al., 1987, Proc. Natl. Acad. Sci. U.S.A 84, 5409-13; Quill, H. & Schwartz, R H., 1987, J. Immunol. 138, 3704-3712; Jenkins, M. K. et al., 1990, J. Immunol. 144, 16-22). Additionally, it constitutes one means of imposing peripheral tolerance. Anergic T cells are functionally inactive and unable to initiate a productive immune response even when the antigen is encountered in the presence of full costimulation. Anergic CD4$^+$ T cells with distinct phenotypic and gene-expression programs can even convert into regulatory T cells that, in turn, can promote anergy of pathogenic CD4$^+$ T cells and inhibit autoimmunity (Kalekar, L. A. et al., 2016, Nat. Immunol. 17, 304-14). Lag-3, Tim-3, ICOS as well as TIGIT mediate co-inhibitory functions on effector T cells and an overexpression of these molecules is associated with T cell exhaustion (Anderson, A. C. et al., 2016, Immunity 44, 989-1004). The accumulation of multiple co-inhibitory receptors on the surface of T cells is even associated with increased dysfunction (Blackburn, S. D. et al., 2009, Nat. Immunol. 10, 29-37). TIGIT itself acts as a co-inhibitory molecule by directly down regulating the proliferation of T cells, but also by preventing DCs maturation, decreasing IL-12 secretion and inducing the production of the immunosuppressive cytokine IL-10 (Yu, X. et al., 2009, Nat. Immunol. 10, 48-57; Joller, N. et al., 2011, J. Immunol. 186, 1338-1342). Lag-3 plays a role in the modulation of T cell homeostasis and effector T cell responses (Workman, C. J. et al., 2002, J. Immunol. 169, 5392-5395; Workman, C. J. & Vignali, D. A. A., 2003, Eur. J. Immunol. 33, 970-979; Workman, C. J. & Vignali, D. A. A., 2005, J. Immunol. 174, 688-695).

Furthermore, immune checkpoint molecules like programmed death 1 receptor (PD-1) and cytotoxic T lymphocyte-associated protein 4 (CTLA-4) are co-inhibitory molecules involved in the negative regulation of immune responses and consequently the maintenance of peripheral self-tolerance. Co-inhibitory molecules are in general upregulated upon T cell activation and constrain the effector response through feedback inhibition. PD-1 and its ligands, PD-L1 and PD-L2 for example deliver inhibitory signals that regulate the balance between T cell activation and tolerance (Keir, M. E. et al., 2008, Annu. Rev. Immunol. 26, 677-704). Immune responses to self-antigens require specific and balanced responses to maintain tolerance, which is mediated by the different co-inhibitory receptors and its ligand.

By an upregulation of PD-1 effector T cell responses will be shut off and tissues are in turn protected from immune cell-mediated damage.

All these co-inhibitory receptors play a central role in regulating autoimmune diseases and deficiency in some of these molecules even leads to autoimmunity.

Example 9: More Detailed Characterization of MOG35-55 Specific $CD4^+$ T Cells Upon Non-Immunogenic Antigen-Specific mRNA Treatment in the Disease Model EAE In accordance with the results shown in Example 6, FIGS. 8 and 9 also adoptive cell transfer experiments of MOG35-55 specific $CD4^+$ T cells showed the same results. MOG35-55 specific $Thy1.1^+CD4^+$ T cells of 2D2 TCR transgenic mice were transferred into $Thy1.2^+$ C57BL/6 mice and 24 h later EAE was induced in the recipient mice. On day 7 and 10 after disease induction, mice were treated with 20 μg non-immunogenic MOG35-55-coding mRNA, 20 μg non-immunogenic irrelevant mRNA or saline. Six days after the last mRNA treatment, brain and spinal cord were isolated. Cells from these tissues were reactivated in vitro with MOG35-55 peptide for 6 h and then gated on $Thy1.1^+ CD4^+$ T cells. As depicted in FIG. 16, administration of non-immunogenic MOG35-55 coding mRNA led to significant decrease in the frequency of MOG35-55-specific $CD4^+$ T cells in the brain and spinal cord. On the functional level, $CD4^+$ T cells secrete significantly less IFNγ and Interleukin-17A (IL-17A) in the brain and spinal cord of mice treated with non-immunogenic MOG35-55 coding mRNA compared to control mice (FIG. 17). These data again indicate that mRNA treatment with non-immunogenic MOG35-55 mRNA can inactivate Teff cells, leading to a reduced infiltration of these cells into the brain and spinal cord.

To investigate the antigen-specific CD4 T cell phenotype after successful treatment, EAE was actively induced and on day 7 and day 10 after disease induction animals were treated with 20 μg non-immunogenic MOG35-55 coding mRNA, 20 μg non-immunogenic irrelevant mRNA or saline. At the peak of the disease (day 16 after disease induction), the CD4 T cell phenotype in the spleen was investigated by MOG35-55 tetramer staining. In accordance with the experiments shown in Example 5 and 8, also in the EAE disease setting, the antigen-specific tolerance induced by non-immunogenic antigen-specific mRNA is mediated by the upregulation of co-inhibitory molecules Lag-3, ICOS, TIGIT and Tim-3 on MOG35-55 specific $CD4^+$ T cells in the spleen (FIG. 18A). Besides the cell-intrinsic mechanism mediating immune tolerance like anergy and negative costimulation, also cell-extrinsic (Treg cell mediated tolerance) mechanisms can mediate the non-immunogenic antigen-specific mRNA treatment effect. As already discussed, Tregs play a crucial role in antigen-specific tolerance (Sakaguchi, S. et al., 1985, J. Exp. Med. 161, 72-87). FACS analysis of MOG35-55 specific $CD4^+$ T cells furthermore showed significant expansion of Treg populations (FIG. 18B). Additionally, Tregs in the spleens of mice treated with antigen-specific non-immunogenic mRNA express high levels of CD69, indicating that they are highly activated.

In order to determine whether the expression of negative costimulatory molecules was required for tolerance induction and maintenance, PD-1 or CTLA-4 were blocked during mRNA treatment of EAE. EAE treatment at day 7 and day 10 after disease induction with non-immunogenic MOG35-55 coding mRNA in combination with anti-PD-1 or anti-CTLA-4 antibody led to reversal of protection from EAE in comparison to mice treated with non-immunogenic MOG35-55 coding mRNA in combination with IgG controls (FIG. 19). This demonstrates that PD-1 and CTLA-4 are crucial for long-term maintenance of antigen-specific tolerance induced by non-immunogenic antigen-specific mRNA, as antibody blockage of PD-1 and CTLA-4 in parallel to mRNA treatment resulted in a marked reduction in the efficacy of tolerance induction mediated by non-immunogenic antigen-specific mRNA treatment.

Taken together, the depicted experiments investigated the mode of action of this new therapeutic approach of antigen-specific tolerance induction by treatment with antigen-specific non-immunogenic mRNA. The results show that antigen-specific non-immunogenic mRNA treatment is an effective method of altering harmful immune responses in autoimmunity to confer protection. The experiments shown in naïve as well as in disease-afflicted mice demonstrate that the treatment with non-immunogenic antigen-specific mRNA results in the induction of anergic and regulatory T cells that mediate tolerance in the periphery, leading to a successful treatment of an ongoing autoimmune disease. It was shown that the therapeutic effect relies on already well-described mechanisms for tolerance induction as described in the literature discussed in each example. These mechanisms are important and fundamental for tolerance induction independent of the type of autoimmune disease. The mechanism of tolerance mediated by non-immunogenic antigen-specific mRNA treatment can thus be transferred to any other type of autoimmune disease.

Example 10: Antigen-Specific Tolerance Induction by Treatment with Non-Immunogenic Antigen-Specific mRNA is Independent of the EAE Disease Model All previously described EAE experiments were performed in C57BL/6 mice induced with MOG35-55 peptide resulting in a monophasic disease progression. Another model of EAE is characterized by recurrent disease due to a different relevant epitope (PLP139-151) leading to a relapsing-remitting disease course in SJL mice. This model was employed to demonstrate tolerance induction in a more clinically relevant disease setting. FIG. 20A shows that mRNA treatment 2× per week starting from day 7 and day 10 after EAE induction with non-immunogenic PLP139-151 coding mRNA in the relapsing-remitting disease model has a positive effect on the EAE development as these mice showed a much weaker disease progression than mice treated with non-immunogenic irrelevant control mRNA. To even better simulate the situation in MS, a complex EAE associated with multiple pathogenic autoreactive T cell clones, was used. Since upon a definite diagnosis of MS, the disease is likely already associated with complex anti-myelin autoreactivity, due to "epitope spread" the efficacy of multi-epitope treatment approach was investigated. As shown in FIG. 20B, the complex EAE was successfully treated by a mix of four different non-immunogenic disease-epitope coding mRNAs coding for MOG35-55, PLP139-151, PLP178-191 and MBP84-104. Of each non-immunogenic disease-epitope coding mRNA 10 µg was used, resulting in 40 µg for the efficient treatment. None of the single epitope treatments was able to confer similar treatment outcomes, as shown for 20 µg non-immunogenic MOG35-55 coding mRNA.

These results show that the antigen-specific tolerance induction observed in the different experiments is independent of a specific epitope and can be mediated with different disease relevant epitopes. Furthermore, the data underline that even a complex ongoing disease with a complex pathogenic autoimmune process can be successfully treated by administration of multiple non-immunogenic myelin-specific mRNA constructs.

Example 11: Co-Delivery of Immunomodulatory Cytokines Improves the Tolerogenic Effect of Non-Immunogenic Antigen-Specific mRNA-LPX Treatment Several immunoregulatory molecules, such as IL-10 can support Treg function. Furthermore the anti-inflammatory cytokine IL-10 is known to induced tolerogenic DCs (Torres-Aguilar, H. et al., 2010, Autoimmun. Rev. 10, 8-17; Torres-Aguilar, H. et al., 2010, J. Immunol. 184, 1765-1775; Steinbrink K. et al., 1997, J. Immunol. 159, 4772-4780) and to suppress T cell proliferation and cytokine responses (Gu, Y. et al., 2008, Eur. J. Immunol. 38, 1807-1813; Guo, B., 2016, J. Clin. Cell Immunol. 7, 1-16). Also IL-27 is a cytokine know to have anti-inflammatory properties and in EAE studies, it has been shown that this cytokine dampens the severity of the disease (Mascanfroni, I. D. et al., 2013, Nat. Immunol. 14, 1054-63; Thom, R. et al., 2017, Front. Immunol. 8, 1-14). In a set of EAE experiments the co-delivery of non-immunogenic antigen-specific mRNA with immunomodulatory cytokines like IL-10 and IL-27 encoded by non-immunogenic mRNA should be investigated in regard to modulate the immune response and improve the efficiency of tolerance induction.

The ability of co-delivery of immunomodulatory cytokines to enhance the tolerogenicity of single-antigen-specific mRNA-LPX treatment was evaluated using a 'subtherapeutic' treatment of EAE mice. Non-immunogenic antigen-specific mRNA-LPX treatment has demonstrated robust tolerance induction in the previous experiments, therefore the combinatorial approach of additional non-immunogenic cytokine-coding mRNA treatment was investigated in the EAE model at subtherapeutic doses to identify therapeutic contributions.

To investigate the beneficial effect of non-immunogenic cytokine-coding mRNA treatment on non-immunogenic antigen-specific mRNA in the disease model, EAE was actively induced in C57BL/6 mice and mice were treated at day 7 and day 10 after disease induction with non-immunogenic antigen-specific MOG35-55 coding mRNA, non-immunogenic MOG35-55 coding mRNA in combination with non-immunogenic mIL-10 (FIG. 21A) or mIL-27 (FIG. 21B) coding mRNA, non-immunogenic cytokine-coding mRNA alone, as well as non-immunogenic irrelevant mRNA.

The results depicted in FIG. 21 suggest that co-delivery of immunomodulatory cytokines encoded by non-immunogenic mRNA enhances tolerance in an antigen-specific context. Furthermore, it does not broadly suppress the immune response as single cytokine-coding mRNA treatment showed no changes on EAE progression in comparison to control mice.

The invention claimed is:

1. A method of treating an autoimmune disease in a subject,
   comprising administering to the subject a composition comprising a non-immunogenic RNA encoding a peptide or polypeptide comprising an autoantigen or a fragment thereof, or a variant of the autoantigen or fragment, wherein the non-immunogenic RNA comprises 1-methyl-pseudouridine, wherein the non-immunogenic RNA is formulated in a F12 liposome, and wherein the composition does not comprise dsRNA.

2. A method of inducing tolerance to autoreactive T cells in a subject, comprising administering to the subject a composition comprising a non-immunogenic RNA encoding a peptide or polypeptide comprising an autoantigen or a fragment thereof, or a variant of the autoantigen or fragment, wherein the non-immunogenic RNA comprises 1-methyl-pseudouridine, wherein the non-immunogenic RNA is formulated in a F12 liposome, and wherein the composition does not comprise dsRNA.

3. The method of claim 2, wherein the subject has an autoimmune disease.

4. The method of claim 2, wherein the non-immunogenic RNA when administered does not result in activation of dendritic cells, activation of T cells and/or secretion of IFN-alpha.

5. The method of claim 2, wherein the non-immunogenic RNA is mRNA or in vitro transcribed RNA.

6. The method of claim 2, wherein the autoantigen is a T cell-antigen, CNS-derived, a myelin antigen, or Myelin Oligodendrocyte Glycoprotein (MOG).

7. The method of claim 2, wherein the peptide or polypeptide comprising an autoantigen or a fragment thereof, or a variant of the autoantigen or fragment comprises amino acids 35 to 55 of Myelin Oligodendrocyte Glycoprotein (MOG).

8. The method of claim 2, wherein the non-immunogenic RNA is formulated in a delivery vehicle.

* * * * *